(12) United States Patent
Révész

(10) Patent No.: US 6,608,072 B1
(45) Date of Patent: Aug. 19, 2003

(54) THIAZOLE COMPOUNDS AND THEIR PHARMACEUTICAL USE

(75) Inventor: László Révész, Therwil (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/111,233

(22) PCT Filed: Oct. 25, 2000

(86) PCT No.: PCT/EP00/10528

§ 371 (c)(1),
(2), (4) Date: Apr. 22, 2002

(87) PCT Pub. No.: WO01/30778

PCT Pub. Date: May 3, 2001

(30) Foreign Application Priority Data

Oct. 27, 1999 (GB) .............................. 9925441
Nov. 4, 1999 (GB) .............................. 9926173

(51) Int. Cl.$^7$ ............ C07D 417/04; A61K 31/437
(52) U.S. Cl. ........... 514/275; 514/318; 514/342; 544/315; 544/331; 544/332; 546/194; 546/270.4
(58) Field of Search ................ 544/315, 331, 544/333; 546/194, 270.4; 514/275, 318, 342

(56) References Cited

U.S. PATENT DOCUMENTS 5,739,143 A    4/1998   Adams et al. ............... 544/275

FOREIGN PATENT DOCUMENTS

| WO | WO 95/13067 A | | 5/1995 |
| WO | WO 97/05878 A | | 2/1997 |
| WO | WO 99/21555 | * | 5/1999 |
| WO | WO 00/09506 A | | 2/2000 |
| WO | WO 00/63204 A | | 10/2000 |
| WO | WO 00/64894 A | | 11/2000 |
| WO | WO 00/69848 A | | 11/2000 |

OTHER PUBLICATIONS

Rasmussen, PubMed Abstract (Dan Med Bull 47(2): 94–114), Apr. 2000.*

* cited by examiner

Primary Examiner—Deepak Rao
(74) Attorney, Agent, or Firm—Carol A. Loeschorn; D. Gabrielle Brouillette

(57) ABSTRACT

Compounds of formula (I) and pharmaceutically-acceptable and -cleavable esters thereof and acid addition salts thereof, wherein the symbols are as defined are MAP kinase inhibitors, useful pharmaceutically for treating TNFα and IL-1 mediated diseases such as rheumatoid arthritis and diseases of bone metabolism, e.g. osteoporosis.

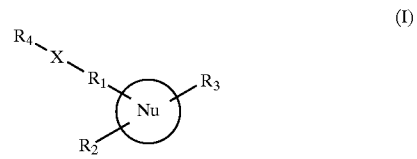

(I)

10 Claims, No Drawings

THIAZOLE COMPOUNDS AND THEIR PHARMACEUTICAL USE

This is a 371 of International Application PCT/EP00/10528, filed Oct. 25, 2000 and published in English, the contents of which are incorporated herein by reference.

This invention relates to heterocyclic compounds, in particular to thiazoles and imidazopyridines and to their use for treating TNFα and IL-1 mediated diseases such as rheumatoid arthritis and diseases of bone metabolism, e.g. osteoporosis.

Accordingly the present invention provides a compound of formula I

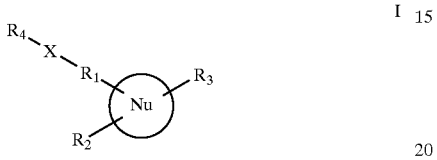

wherein Nu is a heterocyclic nucleus selected from a thiazole in which the $R_1$, $R_2$ and $R_3$ substituents are disposed as indicated below

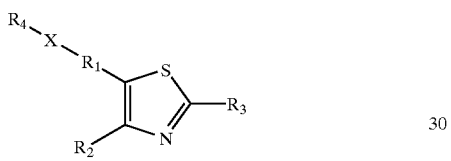

and an imidazo[4,5-b]pyridine in which the $R_1$, $R_2$ and $R_3$ substituents are disposed as indicated below

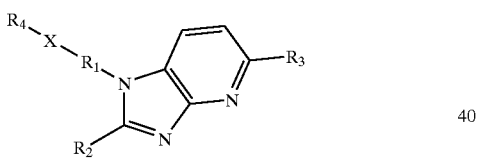

wherein
$R_1$ is pyrimidyl or pyridyl;
X is —$NR_6$—Y—, —O— or —S—,
where $R_6$ is H, $C_1$–$C_4$alkyl, $C_3$–$C_8$cycloalkyl, $C_3$–$C_8$cycloalkyl$C_1$–$C_3$alkyl, $C_6$–$C_{18}$aryl, $C_3$–$C_{18}$heteroaryl, $C_7$–$C_{19}$aralkyl or $C_4$–$C_{19}$heteroaralkyl, and —Y— is $C_1$–$C_4$alkylene or a direct bond;
$R_2$ is phenyl, optionally substituted by one or more substituents, each of which is independently selected from
halo,
$CF_3$,
cyano,
amido or thioamido which is optionally mono- or di-N-substituted by $C_1$–$C_4$alkyl or the N atom of which forms a 5–7 membered heterocyclic ring optionally containing an additional hetero atom selected from O, S or N which N is optionally $C_1$–$C_4$alkyl $C_1$–$C_4$alkylcarbonyl or $C_1$–$C_4$alkylthiocarbonyl substitued,
carboxylate or thiocarboxylate optionally in the form of an optionally halo-substituted $C_1$–$C_{10}$alkoxy, $C_2$–$C_{10}$alkenoxy, $C_2$–$C_{10}$alkynoxy, $C_3$–$C_7$cyclalkoxy, $C_5$–$C_7$cycloalkenoxy, aryloxy, arylalkoxy, heteroaryloxy or heteroarylalkoxy ester,
optionally mono- or di-$C_1$–$C_4$alkyl-substituted-$C_0$–$C_1$alkyl optionally $C_1$–$C_4$alkyl- or $C_3$-$C_5$ cycloalkyl-substituted-carbonyl or -thiocarbonyl,
optionally halo-substituted-$C_1$–$C_4$alkoxy, $C_2$–$C_4$alkenoxy, $C_2$–$C_4$alkynoxy, $C_3$–$C_5$cycloalkoxy or $C_3$–$C_5$cyclothioalkoxy,
optionally halo substituted $C_1$–$C_4$ alkyl,
oxycarbonyl or optionally N—$C_1$–$C_4$alkyl-substituted aminocarbonyl both of which are optionally $C_1$–$C_4$alkyl or $C_3$–$C_5$cycloalkyl substituted (including thiocarbonyl analogues thereof),
optionally mono- or di-$C_1$–$C_4$alkyl-substituted-$C_0$–$C_1$alkylamine which is optionally mono- or di-N—$C_1$–$C_4$ alkyl substituted,
optionally mono- or di-$C_1$–$C_4$acyl-substituted-$C_0$–$C_1$alkyl optionally N—$C_1$–$C_4$alkyl-substituted amino-carbonyl or -thiocarbonyl,
optionally N—$C_1$–$C_4$alkyl-substituted aminosulphinyl or -sulphonyl optionally substituted by
optionally mono- or di-N—$C_1$–$C_4$alkyl-substituted amino,
a nitrogen atom which form a heterocyclic ring of 5 to 7 members optionally containing an additional heteroatom selected from O, S or N which N is optionally $C_1$–$C_4$alkyl $C_1$–$C_4$alkylcarbonyl or $C_1$–$C_4$alkylthiocarbonyl substitued, or
sulphinyl or sulphonyl optionally substituted by
optionally halo-substituted-$C_1$–$C_4$alkyl, $C_2$–$C_4$ alkenyl, $C_2$–$C_4$ alkynyl,
optionally mono- or di-$C_1$–$C_4$alkyl-substituted amino,
a nitrogen atom which form a heterocyclic ring of 5 to 7 members optionally containing an additional heteroatom selected from O, S or N which N is optionally $C_1$–$C_4$alkyl $C_1$–$C_4$alkylcarbonyl or $C_1$–$C_4$alkylthiocarbonyl substitued;
$R_3$ is H, amino, $C_1$–$C_{10}$alkyl, $C_3$–$C_{10}$cycloalkyl, $C_3$–$C_{18}$heterocycloalkyl, $C_6$–$C_{18}$aryl, or $C_3$–$C_{18}$heteroaryl each of which is optionally substituted by up to 4 substituents separately selected from $C_1$–$C_4$alkyl, halogen, halo-substitued-$C_1$–$C_4$alkyl, hydroxy, $C_1$–$C_4$alkoxy, $C_1$–$C_4$alkylthio, $C_6$–$C_{18}$aryl, $C_3$–$C_{18}$ heteroaryl, $C_6$–$C_{18}$aryl$C_1$–$C_4$alkyl, $C_3$–$C_{18}$ heteroaryl$C_1$–$C_4$alkyl, $C_3$–$C_{18}$heterocycloalkyl or optionally mono- or di-$C_1$–$C_4$alkyl substituted amino or by N-heterocyclyl containing from 5 to 7 ring atoms and optionally a further hetero atom selected from O, S or N, all of which are further optionally substituted halo, hydroxy, $C_1$–$C_4$alkyl, $C_1$–$C_4$alkoxy or $C_1$–$C_4$alkoxycarbonyl;
$R_4$ is $C_1$–$C_{10}$alkyl, $C_6$–$C_{18}$aryl, $C_3$–$C_{18}$heteroaryl, or $C_3$–$C_{12}$cycloalkyl optionally substituted by up to 3 substituents separately selected from $C_1$–$C_4$alkyl, halogen, halo-substitued-$C_1$–$C_4$alkyl, hydroxy, $C_1$–$C_4$alkoxy, $C_1$–$C_4$alkylthio, optionally mono- or di-$C_1$–$C_4$alkyl substituted amino, or by N-heterocyclyl containing from 5 to 7 ring atoms and optionally containing a further hetero atom selected from O, S or N,
and pharmaceutically-acceptable and -cleavable esters thereof and acid addition salts thereof.

Above and elsewhere in the present description the terms halo or halogen denote I, Br, Cl or F.

Above and elsewhere in the present description the terms such as "$C_3$–$C_{18}$heteroaryl, $C_4$–$C_{19}$heteroaralkyl and $C_3-C_{18}$heterocycloalkyl" denote heteroaryl, heteroaralkyl or heterocycloalkyl substituents comprising at least 3 ring atoms, at least one of which is a hetero atom, e.g. N, O or S, and which in the case of $C_4-C_{19}$heteroaralkyl groups are attached via an alkylene moiety comprising at least 1 carbon atom.

In particular embodiments the invention provides a compound of formula II

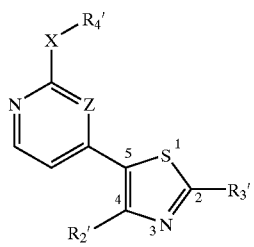

II wherein

Z is N or CH;

X is —$NR_6$—Y—, —O— or —S—,
where $R_6$ is H, $C_1-C_4$alkyl, $C_3-C_8$cycloalkyl, $C_3-C_8$cycloalkyl$C_1-C_3$alkyl, $C_6-C_{18}$aryl, $C_3-C_{18}$heteroaryl, $C_7-C_{19}$aralkyl or $C_4-C_{19}$heteroaralkyl, and —Y— is $C_1-C_4$alkylene or a direct bond;

$R_2'$ is phenyl, optionally substituted by one or more substituents, each of which is independently selected from halo, $CF_3$, cyano, amido or thioamido, carboxylate or thiocarboxylate, $C_1-C_4$alkoxy, $C_1-C_4$alkyl, or $NH_2$ which is optionally mono- or di-$C_1-C_4$ alkyl substituted;

$R_3'$ is H, $C_1-C_{10}$alkyl, $C_3-C_{10}$cycloalkyl, $C_3-C_{18}$heterocycloalkyl, $C_6-C_{18}$aryl, or $C_3-C_{18}$heteroaryl each of which is optionally substituted by up to 4 substituents separately selected from $C_1-C_4$alkyl, halogen, halo-substitued-$C_1-C_4$alkyl, hydroxy, $C_1-C_4$alkoxy, $C_1-C_4$alkylthio, or optionally mono- or di-$C_1-C_4$alkyl substituted amino, or by N-heterocyclyl containing from 5 to 7 ring atoms and optionally containing a further hetero atom selected from O, S or N;

$R_4'$ is $C_6-C_{18}$aryl, $C_3-C_{18}$heteroaryl, or $C_3-C_{12}$cycloalkyl each of which is optionally substituted by up to 4 substituents separately selected from $C_{1-4}$alkyl, halogen, halo-substitued-$C_{1-4}$alkyl, hydroxy, $C_{1-4}$alkoxy, $C_{1-4}$alkylthio, or optionally mono- or di-$C_1-C_4$alkyl substituted amino, or by N-heterocyclyl containing from 5 to 7 ring atoms and optionally containing a further hetero atom selected from O, S or N, and pharmaceutically-acceptable and -cleavable esters thereof and acid addition salts thereof.

When $R_3'$ is aryl, it is preferably heteroaryl, e.g. pyridyl (e.g. 4-pyridyl) or pyrazyl, each optionally substituted, e.g. by 2 substituents, separately selected from $C_1-C_4$alkyl, halogen, hydroxy, $C_1-C_4$alkoxy, or optionally mono- or di-$C_1-C_4$alkyl substituted amino.

When $R_3'$ is cycloalkyl it is preferably $C_3-C_8$, especially $C_5-C_6$cycloalkyl (e.g. cyclohexyl), optionally substituted, e.g. by 1 or 2 substituents, separately selected from $C_1-C_4$alkyl, halogen, hydroxy, $C_1-C_4$alkoxy, or optionally mono- or di-$C_1-C_4$alkyl substituted amino.

When $R_3'$ is heterocycloalkyl it is preferably N-heterocyclyl containing from 5 to 7 ring atoms and optionally containing a further hetero atom, e.g. N or O, and is optionally substituted, e.g. by 1 or 2 substituents, separately selected from $C_1-C_4$alkyl, halogen, hydroxy, $C_1-C_4$alkoxy, or optionally mono- or di-$C_1-C_4$alkyl substituted amino.

When $R_4'$ is aryl it is preferably phenyl. When $R'_4$ is cycloalkyl, it is preferably $C_3-C_7$ cycloalkyl, e.g. cyclopropyl, cyclopentyl, cyclohexyl or cycloheptyl. $R'_4$ may be unsubstituted or substituted, conveniently monosubstituted, e.g. phenyl conveniently meta or para substituted, by halogen, $C_1-C_4$alkyl, halo-substitued$C_1-C_4$alkyl, $C_1-C_4$alkoxy, hydroxy or optionally mono- or di-$C_1-C_4$alkyl substituted amino, or by N-heterocyclyl containing from 5 to 7 ring atoms and optionally containing a further hetero atom selected from O, S or N.

When Y is $C_1-C_4$ alkylene, it is preferably $C_1-C_2$ alkylene, and is optionally substituted, e.g. by $C_1-C_4$alkyl (e.g. methyl), halogen, hydroxy, $C_1-C_4$alkoxy, or amino.

More preferably $R'_2$ is phenyl substituted, preferably mono- or di-substituted, by halogen or a halogen-containing group, e.g. 4-fluorophen-1-yl, or 3-$CF_3$, 3-Cl, or 3,4-difluoro substituted phenyl.

More preferably $R'_3$ is H, $C_1-C_6$alkyl, phenyl, pyridyl, morpholinyl, piperidyl, piperazyl, or optionally mono- or di-$C_{1-4}$alkyl substituted amino, each of which is optionally substituted, e.g. by up to 2 substituents, separately selected from $C_1-C_4$alkyl, halogen, hydroxy, $C_1-C_4$alkoxy, or optionally mono- or di-$C_1-C_4$alkyl substituted amino.

Preferably X is —NH—Y'—, —O— or —S—, where Y' is —$CH_2$—, —$CH_2$—$CH_2$—, —$CH(CH_3)$— or a direct bond Thus in preferred embodiments the invention provides a compound of formula II'

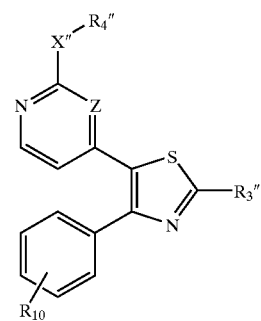

II' wherein $R_4''$ is phenyl or $C_3-C_7$cycloalkyl each of which is optionally mono-substituted by halogen, $C_1-C_4$alkyl, $C_1-C_4$alkoxy, hydroxy, trihalomethyl or optionally mono- or di-$C_1-C_4$alkyl substituted amino, or by N-heterocyclyl containing from 5 to 7 ring atoms and optionally containing a further hetero atom selected from O, S or N;

$R_{10}$ is halogen, cyano, amido, thioamido, amino or $C_1-C_4$alkyl;

$R_3''$ is H, $C_1-C_4$alkyl, phenyl, pyridyl, morpholinyl, piperidyl, piperazyl, or optionally mono- or di-$C_{1-4}$alkyl substituted amino, each of which is optionally substituted, e.g. by up to 2 substituents, separately selected from $C_1-C_4$alkyl, halogen, hydroxy, $C_1-C_4$alkoxy, or optionally mono- or di-$C_1-C_4$alkyl substituted amino;

Z is N or CH and

X" is —NH—Y'—, —O— or —S—, where Y' is —CH₂—, —CH₂—CH₂—, —CH(CH₃)— or a direct bond,
and pharmaceutically-acceptable and -cleavable esters thereof and acid addition salts thereof.

Preferably R₄" is unsubstituted or monosubstituted by halogen, C₁–C₄alkyl (e.g. methyl), C₁–C₄alkoxy (e.g. methoxy), hydroxy or CF₃.

Preferably R₁₀ is halogen, e.g. F.

Preferably X" is —NH—Y' where Y' is —CH(CH₃)—.

The Invention includes the following compounds:
4-(4-Fluorophenyl)-5-(2-[1-(S)-phenylethyl]amino-4-pyrimidinyl)-2-(4-methyl-piperidine-1-yl)thiazole;
4-(4-Fluorophenyl)-5-(2-[1-(S)-phenylethyl]amino-4-pyrimidinyl)-2-(4-NH-piperidine-1-yl)thiazole;
4-(4-Fluorophenyl)-2-(4-methylpiperidine-1-yl)-5-(2-[cyclopropyl-methyl]amino-4-pyridinyl)thiazole and
4-(4-Fluorophenyl)-2-(4-NH-piperidine-1-yl)-5-(2-(1-(S)-phenylethyl)amino-4-pyridinyl)thiazole;

The novel thiazoles of the invention, in particular the compounds of formulae II and II' and the specific compounds listed above are hereinafter referred to "Agents of the Invention".

Agents of the Invention of formula II"

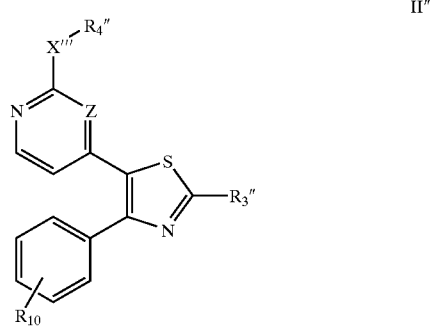

II"

wherein R₃", R₅", R₁₀ and Z are as previously defined and X'" is —NH—, may be prepared by reacting the corresponding precursor compound of formula III or III'

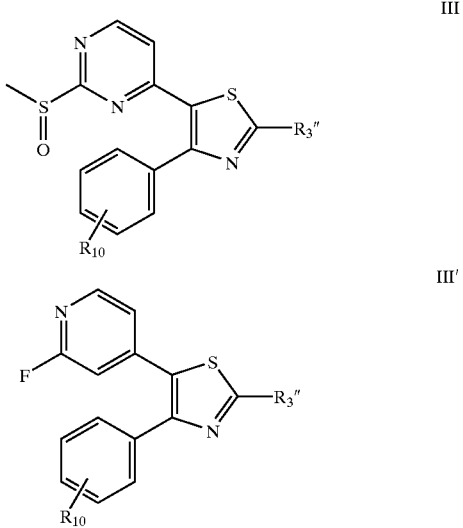

III

III' wherein R₃' and R₁₀ are as previously defined, with the corresponding R₄"—NH₂ derivative. For example, the reaction may be carried out by refluxing the reactants in an organic solvent, e.g. dichloroethane, e.g. in the presence of diethoxytrifluoroborane. Thereafter, if desired, the compound of Formula II" obtained may be converted into a further compound of Formula II" or otherwise treated as required.

The precursor compound of formula III may be prepared by controlled oxidation of the corresponding 5(2-methylthio-4-pyrimidinyl)-4-phenythiazole, e.g. employing an oxidising agent such as mCPBA (meta chloroperbenzoic acid), conveniently in an organic solvent such as methylene chloride. The corresponding 5(4-pyrimidinyl/pyridinyl)-4-phenylthiazole compound may be prepared by contacting the corresponding acetophenone precursor compound of formula IV or IV'

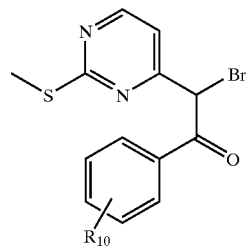

IV

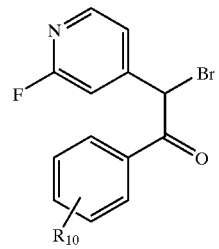

IV' wherein R₁₀ is as defined above, with a corresponding thioamide of formula R₃'C(S)NH₂, typically at elevated temperature. The compounds of formula IV and IV' may be prepared by bromination of the corresponding acetophenone, e.g. 2-(2-methylthio-4-pyrimidinyl) acetophenone. The acetophenone precursor may be prepared by reacting the corresponding N-methoxy-N-methylbenzamide with the corresponding pyrimidine, e.g. 4-methyl-2-(methylthio)pyrimidine, for instance in a THF containing organic solvent with cooling.

Thus in a further aspect the invention includes a process for the preparation of a compound of formula II"

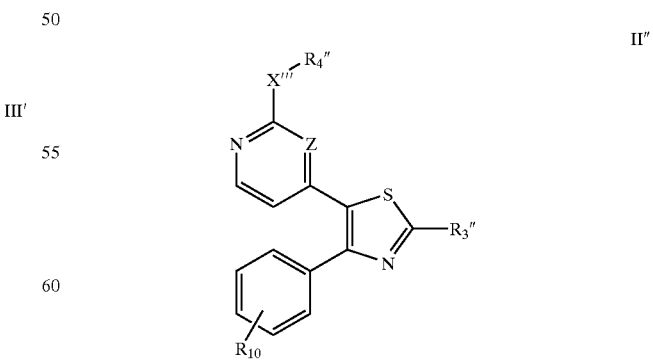

II"

wherein R₃", R₄", R₁₀ and Z are as previously defined and X'" is —NH—, which comprises reacting the corresponding precursor compound of formula III or III'

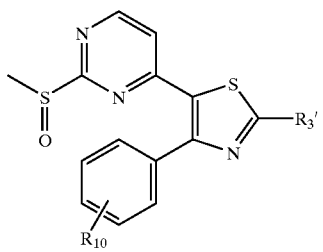

III

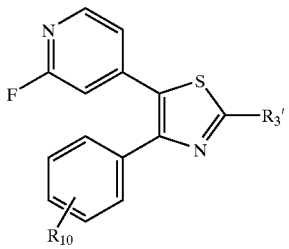

III' wherein $R_3''$ and $R_{10}$ are as previously defined, with the corresponding $R_4''$—$NH_2$ amine, and thereafter, if desired, converting the compound of formula II" obtained into a further compound of formula II" or a pharmaceutically-acceptable and -cleavable ester thereof or acid addition salt thereof.

In further particular embodiments the invention provides a compound of formula V

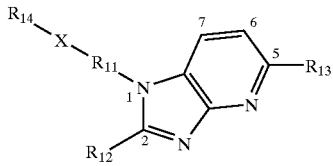

V wherein
$R_{11}$ is pyrimidyl;
X is —$NR_6$—Y—, —O— or —S—,
  where $R_6$ is H, $C_1$–$C_4$alkyl, $C_3$–$C_8$cycloalkyl, $C_3$–$C_8$cycloalkyl$C_1$–$C_3$alkyl, $C_6$–$C_{18}$aryl, $C_3$–$C_{18}$heteroaryl, $C_7$–$C_{19}$aralkyl or $C_4$–$C_{19}$heteroaralkyl, and —Y— is $C_{1-4}$alkylene or a direct bond;
$R_{12}$ is phenyl, optionally substituted by one or more substituents, each of which is independently selected from
  halo,
  $CF_3$,
  cyano,
  amido or thioamido which is optionally mono- or di-N-substituted by $C_1$–$C_4$alkyl or the N atom of which form a 5–7 membered heterocyclic ring optionally containing an additional hetero atom selected from O, S or N which N is optionally $C_1$–$C_4$alkyl $C_1$–$C_4$alkylcarbonyl or $C_1$–$C_4$alkylthiocarbonyl substitued,
  carboxylate or thiocarboxylate optionally in the form of an optionally halo-substituted $C_1$–$C_{10}$alkoxy, $C_2$–$C_{10}$alkenoxy, $C_2$–$C_{10}$alkynoxy, $C_3$–$C_7$cyclalkoxy, $C_5$–$C_7$cycloalkenoxy, aryloxy, arylalkoxy, heteroaryloxy or heteroarylalkoxy ester,
  optionally mono- or di-$C_1$–$C_4$alkyl-substituted- $C_0$–$C_1$alkyl optionally $C_1$–$C_4$alkyl- or $C_3$–$C_5$ cycloalkyl-substituted-carbonyl or -thiocarbonyl,
  optionally halo-substituted-$C_1$–$C_4$alkoxy, $C_2$–$C_4$alkenoxy, $C_2$–$C_4$alkynoxy, $C_3$–$C_5$cycloalkoxy or $C_3$–$C_5$cyclothioalkoxy,
  optionally halo substituted $C_1$–$C_4$ alkyl, oxycarbonyl or optionally N—$C_1$–$C_4$alkyl-substituted aminocarbonyl both of which are optionally $C_1$–$C_4$alkyl or $C_3$–$C_5$cycloalkyl substituted (including thiocarbonyl analogues thereof),
  optionally mono- or di-$C_1$–$C_4$alkyl-substituted- $C_0$–$C_1$alkylamine which is optionally mono- or di-N—$C_1$–$C_4$ alkyl substituted,
  optionally mono- or di-$C_1$–$C_4$alkyl-substituted- $C_0$–$C_1$alkyl optionally N—$C_1$–$C_4$alkyl-substituted amino-carbonyl or -thiocarbonyl,
  optionally N—$C_1$–$C_4$alkyl-substituted amino-sulphinyl or -sulphonyl optionally substituted by
    optionally mono- or di-N—$C_1$–$C_4$alkyl-substituted amino,
    a nitrogen atom which form a heterocyclic ring of 5 to 7 members optionally containing an additional heteroatom selected from O, S or N which N is optionally $C_1$–$C_4$alkyl $C_1$–$C_4$alkylcarbonyl or $C_1$–$C_4$alkylthiocarbonyl substituted, or
  sulphinyl or sulphonyl optionally substituted by
    optionally halo-substituted-$C_1$–$C_4$alkyl, $C_2$–$C_4$ alkenyl, $C_2$–$C_4$ alkynyl,
    optionally mono- or di-N—$C_1$–$C_4$alkyl-substituted amino,
    a nitrogen atom which form a heterocyclic ring of 5 to 7 members optionally containing an additional heteroatom selected from O, S or N which N is optionally $C_1$–$C_4$alkyl $C_1$–$C_4$alkylcarbonyl or $C_1$–$C_4$alkylthiocarbonyl substituted;
$R_{13}$ is H, amino, $C_1$–$C_{10}$alkyl, $C_3$–$C_{10}$cycloalkyl, $C_3$–$C_{18}$heterocycloalkyl, $C_6$–$C_{18}$aryl, or $C_3$–$C_{18}$heteroaryl all optionally substituted by up to 4 substituents separately selected from $C_1$–$C_4$alkyl, halogen, halo-substitued-$C_1$–$C_4$alkyl, hydroxy, $C_1$–$C_4$alkoxy, $C_1$–$C_4$alkylthio, $C_6$–$C_{18}$aryl, $C_3$–$C_{18}$heteroaryl, $C_6$–$C_{18}$aryl$C_1$–$C_4$alkyl, $C_3$–$C_{18}$heteroaryl$C_1$–$C_4$alkyl, $C_3$–$C_{18}$heterocycloalkyl or optionally mono- or di-N—$C_1$–$C_4$alkyl substituted amino all of which are optionally substituted by halo, hydroxy, $C_1$–$C_4$alkyl, $C_1$–$C_4$alkoxy or $C_1$–$C_4$alkoxycarbonyl;
$R_{14}$ is $C_1$–$C_{10}$alkyl, $C_6$–$C_{18}$aryl, $C_3$–$C_{18}$heteroaryl, or $C_3$–$C_{12}$cycloalkyl optionally substituted by up to 3 substituents separately selected from $C_1$–$C_4$alkyl, halogen, halo-substitued-$C_1$–$C_4$alkyl, hydroxy, $C_1$–$C_4$alkoxy, $C_1$–$C_4$alkylthio, optionally mono- or di-N—$C_1$–$C_4$alkyl substituted amino, or by N-heterocyclyl containing from 5 to 7 ring atoms and optionally containing a further hetero atom selected from O, S or N,
and pharmaceutically-acceptable and -cleavable esters thereof and acid addition salts thereof.

$R_{11}$ is preferably 4-pyrimidyl.

When $R_{13}$ is alkyl it is $C_1$–$C_{10}$alkyl, preferably $C_1$–$C_6$alkyl, optionally substituted, preferably with one or two substituents separately selected from hydroxy, $C_1$–$C_4$alkoxy, amino optionally mono- or disubstituted by $C_1$–$C_4$alkyl or N-heterocyclyl containing from 5 to 7 ring and optionally containing a further hetero atom (e.g. O, S or N).

When $R_{13}$ is aryl or heteroaryl either of which is optionally substituted by up to 4 substituents, $R_{13}$ may comprise one of the customary aryl or heteroaryl substituents in the art and may be substituted as is customary in the art; for instance as defined for the substituent $R_3$ of WO 93/03297. For instance, $R_{13}$ may comprise a phenyl, pyridyl or pyrimidyl, substituent optionally substituted by up to 5 substituents separately selected from $C_1$–$C_4$alkyl, halogen, halo-substituted $C_1$–$C_4$alkyl, hydroxy, $C_1$–$C_4$alkoxy, or optionally mono- or di-$C_1$–$C_4$alkyl substituted amino.

When $R_{13}$ is substituted amino it may be substituted by one or two substitutents independently selected from $C_1$–$C_4$alkyl, $C_6$–$C_{18}$aryl, $C_3$–$C_{18}$ heteroaryl, $C_6$–$C_{18}$aryl$C_1$–$C_4$alkyl, $C_3$–$C_{18}$heteroaryl$C_1$–$C_4$alkyl, all of which are optionally substituted by halo, hydroxy, $C_1$–$C_4$alkyl, $C_1$–$C_4$alkoxy or $C_1$–$C_4$alkoxycarbonyl.

When $R_{13}$ is cycloalkyl it is preferably $C_3$–$C_8$, especially $C_5$–$C_6$cycloalkyl (e.g. cyclohexyl), optionally substituted, preferably with up to 2 substituents separately selected from $C_1$–$C_4$alkyl, halogen, hydroxy, $C_1$–$C_4$alkoxy, or optionally mono- or di-$C_1$–$C_4$alkyl substituted amino.

When $R_{13}$ is heterocycloalkyl it is preferably N-heterocyclyl containing from 5 to 7 ring atoms and optionally containing a further hetero atom selected from O, S or N, optionally substituted, e.g. by up to 2 substituents, selected from halogen, hydroxy, alkoxy, or optionally mono- or di-$C_1$–$C_4$alkyl substituted amino. For instance, $R_{13}$ may be an optionally substituted morpholino, piperazyl or piperidyl substituent.

When $R_{14}$ is aryl it is preferably phenyl. When $R_{14}$ is cycloalkyl, it is preferably $C_3$–$C_7$ cycloalkyl, e.g. cyclopropyl, cyclopentyl, cyclohexyl or cycloheptyl. $R_{14}$ may be unsubstituted or substituted, conveniently mono-substituted, e.g. phenyl conveniently meta or para substituted, by halogen, $C_1$–$C_4$alkyl, halo-substitued $C_1$–$C_4$alkyl, $C_1$–$C_4$alkoxy, hydroxy, optionally mono- or di-N—$C_1$–$C_4$alkyl substituted amino, or by N-heterocyclyl containing from 5 to 7 ring atoms and optionally containing a further hetero atom selected from O, S or N.

When —Y— is $C_1$–$C_4$ alkylene, it is preferably $C_1$–$C_2$ alkylene, and is optionally substituted, e.g. by $C_1$–$C_4$alkyl (e.g. methyl), halogen, hydroxy, $C_1$–$C_4$alkoxy, or amino.

Preferably $R_{12}$ is phenyl substituted with 1–3 substituents, preferably mono-substituted, selected from halogen, CN, halo-substituted alkyl, e.g. $CF_3$, $C_1$–$C_4$alkyl, or $C_1$–$C_4$alkoxy. Most preferably $R_2$ is phenyl mono-substituted by halogen, e.g. 4-flurophenyl.

In particular embodiments $R_{13}$ is pyridyl, pyrimidyl, piperazyl, piperidyl, —$NR_9R_{10}$, —$CH_2OH$, —$CH_2NR_{15}R_{16}$, —$CH_2CH_2R_{15}R_{16}$, or Het—$C_{1-4}$alkyl-, wherein $R_9$ and $R_{10}$ are separately selected from H, $C_1$–$C_4$alkyl, $C_6$–$C_{18}$aryl, $C_3$–$C_{18}$ heteroaryl, $C_6$–$C_{18}$aryl$C_1$–$C_4$alkyl, $C_3$–$C_{18}$heteroaryl$C_1$–$C_4$alkyl all of which are optionally substituted by halo, $C_1$–$C_4$alkyl, $C_1$–$C_4$alkoxy, $C_1$–$C_4$alkoxycarbonyl, $R_{15}$ and $R_{16}$ are separately selected from H or $C_1$–$C_4$alkyl, and Het is N-heterocyclyl containing from 5 to 7 ring atoms and optionally containing a further hetero atom (e.g. O, S or N).

Preferably X is —NH—Y'—, —O— or —S—, where Y' is —$CH_2$—, —$CH_2$—$CH_2$—, —$CH(CH_3)$— or a direct bond. Most preferably X is NH—Y"—, where Y" is —CH($CH_3$)— or a direct bond.

Thus in preferred embodiments the invention provides a compound of formula V'

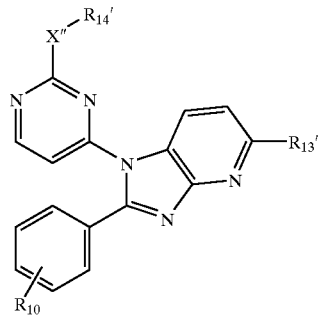

wherein $R_{14}'$ is phenyl or $C_3$–$C_7$cycloalkyl each of which is optionally mono-substituted by halogen, $C_1$–$C_4$alkyl, $C_1$–$C_4$alkoxy, hydroxy, trihalomethyl optionally mono- or di-N—$C_1$–$C_4$alkyl substituted amino, or by N-heterocyclyl containing from 5 to 7 ring atoms and optionally containing a further hetero atom selected from O, S or N;

$R_{10}$ is halogen, $CF_3$, $C_1$–$C_4$alkyl or $C_1$–$C_4$alkoxy;

$R_{13}'$ is pyridyl, pyrimidyl, piperazinyl, piperidinyl, $NR_9R_{10}$, —$CH_2OH$, $CH_2NR_{15}R_{16}$, —$CH_2CH_2R_{15}R_{16}$, or Het—$C_1$–$C_4$alkyl-, wherein $R_9$ and $R_{10}$ are separately selected from H, $C_1$–$C_4$alkyl, $C_6$–$C_{18}$aryl, $C_3$–$C_{18}$ heteroaryl, $C_6$–$C_{18}$aryl$C_1$–$C_4$alkyl, $C_3$–$C_{18}$heteroaryl$C_1$–$C_4$alkyl all of which are optionally substituted by halo, hydroxy, $C_1$–$C_4$alkyl, $C_1$–$C_4$alkoxy, $C_1$–$C_4$alkoxycarbonyl, $R_{11}$ and $R_{12}$ are separately selected from H or $C_1$–$C_6$alkyl, and Het is N-heterocyclyl containing from 5 to 7 ring atoms and optionally containing a further hetero atom (e.g. O, S or N)

X" is —NH—Y'—, —O— or —S—, where Y' is —$CH_2$—, —$CH_2$—$CH_2$—, —$CH(CH_3)$— or a direct bond, and pharmaceutically-acceptable and -cleavable esters thereof and acid addition salts thereof.

Preferably $R_{14}'$ is phenyl or cyclopentyl, cyclobutyl or cyclopropyl.

Preferably $R_{10}$ is halogen.

Preferably X" is —NH—Y" where Y" is —CH($CH_3$)— or a direct bond.

The Invention includes the following compounds:

2-(4-Fluorophenyl)-1-(2-cyclopentylamino-4-pyrimidinyl)-5-(piperidino-N-2-ethyl)imidazo[4,5-b]pyridine;

2-(4-Fluorophenyl)-1-(2-cyclopentylamino-4-pyrimidinyl)-5-(N,N-diethylamino-N-2-ethyl)imidazo[4,5-b]pyridine;

2-(4-Fluorophenyl)-1-(2-cyclopentylamino-4-pyrimidinyl)-5-(morpholino-N-2-ethyl)imidazo[4,5-b]pyridine;

2-(4-Fluorophenyl)-1-(2-cyclopentylamino-4-pyrimidinyl)-5-isopropylamino-N-2-ethyl)imidazo[4,5-b]pyridine;

2-(4-Fluorophenyl)-1-(2-cyclopentylamino-4-pyrimidinyl)-5-(pyrrolidino-N-2-ethyl)imidazo[4,5-b]pyridine;

2-(4-Fluorophenyl)-1-(2-cyclopentylamino-4-pyrimidinyl)-5-(3-pyridyl)imidazo[4,5-b]pyridine;

2-(4-Fluorophenyl)-1-(2-cyclopentylamino-4-pyrimidinyl)-5-(4-pyridyl)imidazo[4,5-b ]pyridine;

2-(4-Fluorophenyl)-1-(2-(1-(S)-phenylethyl)amino-4-pyrimidinyl)-5-aminoimidazo[4,5-b]pyridine;

2-(4-Fluorophenyl)-1-(2-cyclopentylamino-4-pyrimidinyl)-5-aminoimidazo[4,5-b]pyridine;

2-(4-Fluorophenyl)-1-(2-(1-(S)-phenylethyl)amino-4-pyrimidinyl)-5-(4-NH-1-piperazinyl)imidazo[4,5-b]pyridine;

2-(4-Fluorophenyl)-1-(2-cyclopentylamino-4-pyrimidinyl)-5-(4-NH-1-piperazinyl)imidazo[4,5-b]pyridine;

2-(4-Fluorophenyl)-1-(2-cyclobutylamino-4pyrimidinyl)-5-(4-NH-1-piperazinyl)imidazo[4,5-b]pyridine;

2-(4-Fluorophenyl)-1-(2-cyclopropylamino-4-pyrimidinyl)-5-(4-NH1-piperazinyl)imidazo[4,5-b]pyridine;

2-(4-Fluorophenyl)-1-(2-(1-(S)-phenylethyl)amino-4-pyrimidinyl)-5-(4methyl-1-1-piperazinyl)imidazo[4,5-b]pyridine;

2-(4-Fluorophenyl)-1-(2-clopentylamino-4-pyrimidinyl)-5-(4-methyl-1-piperazinyl)imidazo[4,5-b]pyridine;

2-(4-Fluorophenyl)-1-(2-cyclobutylamino-4-pyrimidinyl)-5-(4-methyl-1-piperazinyl)imidazo[4,5-b]pyridine;

2-(4-Fluorophenyl)-1-(2-cyclopropylamino-4-pyrimidinyl)-5-(4-methyl-1-piperazinyl)imidazo[4,5-b]pyridine;

2-(4-Fluorophenyl)-1-(2-(1-(S)-phenylethyl)amino-4-pyrimidinyl)-5-(4-(2-hydroxy-2-methyl)propyl-1-piperazinyl)imidazo[4,5-b]pyridine;

2-(4-Fluorophenyl)-1-(2-cyclopentylamino-4-pyrimidinyl)-5-(4-(2-hydroxy-2-methyl)propyl-1-piperazinyl)imidazo[4,5-b]pyridine;

2-(4-Fluorophenyl)-1-(2-cyclobutylamino-4-pyrimidinyl)-5-(4-(2-hydroxy-2-methyl)propyl-1-piperazinyl)imidazo[4,5-b]pyridine;

2-(4-Fluorophenyl)-1-(2-cyclopropylamino-4-pyrimidinyl)-5-(4-(2-hydroxy-2-methyl)propyl-1-piperazinyl)imidazo[4,5-b]pyridine;

2-(4-Fluorophenyl)-1-(2-cyclopentylamino-4-pyrimidinyl)-5-(4-piperidinyl)imdazo[4,5-b]pyridine;

2-(4-Fluorophenyl)-1-(2-cyclopentylamino-4-pyrimidinyl)-5-(1-methyl-4-piperidinyl)imidazo[4,5-b]pyridine;

2-(4-Fluorophenyl)-1-(2-cyclopentylamino-4-pyrimidinyl)-5-(1-(2-hydroxy-2-methyl)propyl-4-piperidinyl)imidazo[4,5-b]pyridine;

2-(4-Fluorophenyl)-1-(2-cyclopentylamino-4-pyrimidinyl)-5-(benzylamino)imidazo[4,5-b]pyridine;

2-(4-Fluorophenyl)1-(2-cyclopentylamino-4-pyrimidinyl)-5-(morpholino)imidazo[4,5-b]pyridine;

2-(4-Fluorophenyl)-1-(2-cyclopentylamino-4-pyrimidinyl)-5-(3-fluorophenyl amino)imidazo[4,5-b]pyridine;

2-(4-Fluorophenyl)-1-(2-cyclopentylamino-4-pyrimidinyl)-5-(pyridyl-4-amino)imidazo[4,5-b]pyridine;

2-(4-Fluorophenyl)-1-(2-cyclopentylamino-4-pyrimidinyl)-5-(1-ethoxycarbonyl piperidine-4-amino)imidazo[4,5-b]pyridine, and 2-(4-Fluorophenyl)-1-(2-cyclopentylamino-4-pyrimidinyl)-5-(piperidine-4-amino)imidazo[4,5-b]pyridine.

The novel imidazopyridines of the invention, in particular the compounds of formulae V and V' and the specific compounds listed above are hereinafter also referred to as "Agents of the Invention".

It will be appreciated that certain Agents of the Invention may contain at least 1 assymetric carbon atom; for instance when Y is substituted alkylene, e.g. when Y" is —CH(CH$_3$)— for the compounds of formula II' or V' above. The resulting diastereomers and enantiomers are encompassed by the instant invention. Preferably, however, e.g. for pharmaceutical use in accordance with the invention, the compounds of formula I, are provided in pure or substantially pure epidermic form, e.g. as compositions in which the compounds are present in a form comprising at least 90%, e.g. preferably at least 95% of a single epimer (i.e. comprising less than 10%, e.g. preferably less than 5% of other epimeric forms). Preferred epimeric compounds of formula I are described hereinafter in the Examples.

The Agents of the Invention which comprise free hydroxyl groups may also exist in the form of pharmaceutically acceptable, physiologically cleavable esters, and as such are included within the scope of the invention. Such pharmaceutically acceptable esters are preferably prodrug ester derivatives, such being convertible by solvolysis or cleavage under physiological conditions to the corresponding Agents of the Invention which comprise free hydroxyl groups. Suitable pharmaceutically acceptable prodrug esters are those derived from a carboxylic acid, a carbonic acid monoester or a carbamic acid, advantageously esters derived from an optionally substituted lower alkanoic acid or an arylcarboxylic acid.

Agents of the Invention may also exist in the form of pharmaceutically acceptable salts, and as such are included within the scope of the invention. Pharmaceutically acceptable salts include acid addition salts with conventional acids, for example, mineral acids, e.g., hydrochloric acid, sulfuric or phosphoric acid, or organic acids, for example, aliphatic or aromatic carboxylic or sulfonic acids, e.g., acetic, propionic, succinic, glycolic, lactic, malic, tartaric, citric, ascorbic, maleic, fumaric, hydroxymaleic, pyruvic, pamoic, methanesulfonic, toluenesulfonic, naphthalenesulfonic, sulfanilic or cyclohexylsulfamic acid; also amino acids, such as argiline and lysine. For compounds of the invention having acidic groups, for example, a free carboxy group, pharmaceutically acceptable salts also represent metal or ammonium salts, such as alkali metal or alkaline earth metal salts, e.g., sodium, potassium, magnesium or calcium salts, as well as ammonium salts, which are formed with ammonia or suitable organic amines.

Agents of the Invention of Formula V"

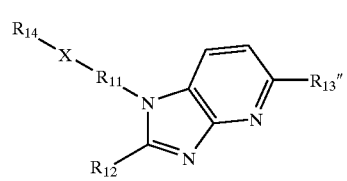

V"

wherein $R_{11}$, $R_{12}$, $R_{14}$ and X are as previously defined and $R_{13}"$ is —CH$_2$—CH$_2$NR$_{15}$R$_{16}$ or —CH$_2$—CH$_2$—Het wherein $R_{15}$, $R_{16}$ and Het are as defined above may be prepared by reacting a corresponding vinyl precursor compound of formula VI

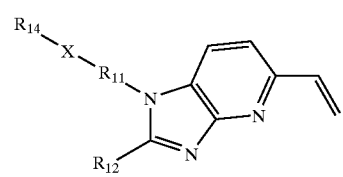

VI wherein $R_{11}$, $R_{12}$, $R_{14}$ and X are as previously defined, with the corresponding amine of formula HNR$_{15}$R$_{16}$ or N-heterocycloalkyl ring compound. For instance the reaction may be carried out by refluxing the reactants, e.g. in acetic acid, followed by treatment with a mild base, e.g. Na$_2$CO$_3$.

The precursor compound of formula VI may be prepared by reacting the corresponding 5-chloro-imdazopyridine of formula VII

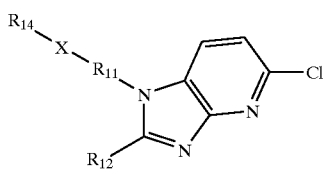

VII wherein $R_{11}$, $R_{12}$, $R_{14}$ and X as are as previously defined, with a vinylating agent. For instance the chloro compound of formula VII is reacted with vinyltributylstannane in the presence of $PdCl_2(PPh_3)_2$ in xylene at elevated temperature, e.g. 160° C., under an inert atmosphere.

Agents of the Invention of formula V, wherein $R_{13}$ is aryl or heteroaryl may be prepared from chloroprecursor compounds of formula VII, as defined above, by arylation or heteroarylation. For instance the compound of formula VII is heated with the corresponding trialkylstannyl-aryl or -heteroaryl, e.g. tributylstannylaryl- or trimethylstannyl-aryl or -heteroaryl, compound e.g. to about 150° C. under an inert atmosphere.

Agents of the Invention of formula V, wherein $R_{13}$ is —N-heterocycloalkyl, —NH-aryl, —NH-heteroaryl, —NH-heterocycloalkyl, —NH—($C_1$–$C_4$alkyl)-heterocycloalkyl, —NH—($C_1$–$C_4$alkyl)-aryl, —NH—($C_1$–$C_4$alkyl)-heteroaryl, or —NH—($C_1$–$C_4$alkyl)-heterocycloalkyl may be prepared from chloroprecursor compounds of formula VII, as defined above, by coupling with the corresponding N-heterocycloalkyl compound or amine. The coupling reaction may carried out using Buchwald chemisty. For instance, to a solution of the chloroprecursor compound of formula VII and a suitable ligand, e.g. BINAP, in an inert organic solvent such as xylene is added the N-heterocycloalkyl compound or amine together with an organic base, e.g. sodium tertiary butylate, and the reaction mixture heated, e.g. to 160° C. for 10 minutes under argon; after which the product may be recovered by pouring the reaction mixture onto water and solvent extraction, e.g. with TBME.

The compounds of formula VII in which X is —NH— may be prepared by reacting the corresponding methylsulphinyl compound of formula VIII

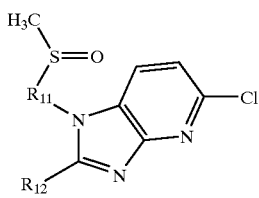

VIII wherein $R_{11}$ and $R_{12}$ are as previously defined, with the corresponding amine of formula $R_{14}$—$NH_2$. For instance, the reactants are mixed and heated, e.g. to 80° C. for 1 h.

The methylsulphinyl compound of formula VIII prepared by oxidation of the corresponding methylthio compound of formula IX.

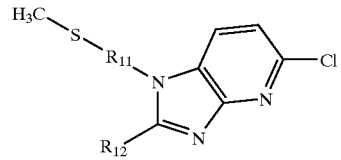

IX wherein $R_{11}$ and $R_{12}$ are as previously defined; for instance, by treating the compound of formula IX in solution, e.g. $CH_2Cl_2$/HOAc solution, with mCPBA, e.g. at 0° C. for 30 min., followed by treatment with mild base, e.g. $Na_2CO_3$.

The methylthio compound of formula IX may be prepared by coupling the corresponding 1-H-imidazopyridine compound of formula X

X wherein $R_{12}$ is as defined above, with 2-methylthio-4-iodopyrimidine. For instance, $KN(TMS)_2$ solution, e.g. in toluene, is added at 0° C. to a solution of X, e.g. in DMF with mixing, and 2-methyl-4-iodopyrimidine solution e.g. in toluene, is added and the reaction mixture heated e.g. at 120° C. for 20 h.

The compound of formula X may be prepared by coupling 2,3-diamino-6-chloropyridine with the corresponding acid of formula $R_{12}$COOH; for instance, by treating a mixture of the reactants with polyphosphonic acid e.g. at 150° C. for 6 h, followed by neutralisation e.g. with cold concentrated aqueous $NH_3$.

Compounds of formula V in which $R_{13}$ is $NH_2$ may be prepared by reacting the corresponding methyl sulphinyl compound of formula VIII'

VIII' wherein $R_{11}$ and $R_{12}$ are as previously defined, with the corresponding amine of formula $R_{14}$—$NH_2$, for instance, as described above for the compound of formula VI. The compound of formula VIII' and precursors therefor may be prepared by analogy with the compound of formula VIII and the precursors thereof; for instance, as described above.

Agents of the Invention which are 5-(4-NH-1-piperazyl) imidazopyridines of formula V in which $R_{13}$ is piperazyl and precursors therefor may be prepared by analogy to the preparation of the compound of formula VIII' and the precursors thereof. Conveniently the free nitrogen atom of the piperazine ring is protected e.g. with a tert. butoxycarbonyl residue, during precursor preparation as appropriate. 5-(4-NH-1-piperazyl)imidazopyridines of formula I may be converted to 5-(4-substituted piperazyl)imidazopyridine Agents of the Invention as desired; for instance, as hereinafter described in the Examples.

Accordingly in a further aspect the invention provides a process for the production of
(i) an Agent of the Invention of formula V''

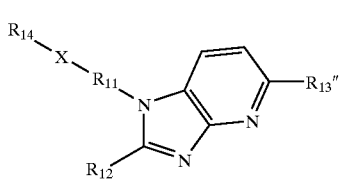

V'' wherein $R_{11}$, $R_{12}$, $R_{14}$ and X are as previously defined and $R_{13}''$ is —$CH_2$—$CH_2NR_{15}R_{16}$ or —$CH_2$—$CH_2$—Het wherein $R_{15}$, $R_{16}$ and Het are as previously defined comprising reacting a corresponding vinyl precursor of formula VI

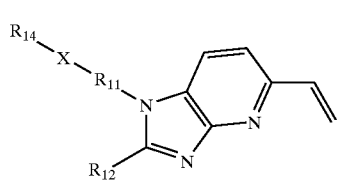

VI wherein $R_{11}$, $R_{12}$, $R_{14}$ and X are as previously defined with the corresponding amine of formula $HNR_{15}R_{16}$ or N-heterocycloalkyl ring compound;

(ii) an Agent of the Invention of formula V wherein $R_{13}$ is Aryl or heteroaryl comprising arylation or heteroarylation of a compound of formula VII

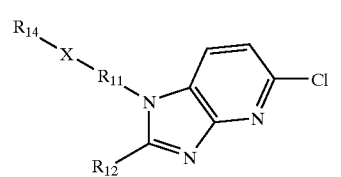

VII wherein $R_{11}$, $R_{12}$, $R_{14}$ and X are as previously defined;

(iii) an Agent of the Invention of formula V wherein $R_{13}$ is —N-heterocycloalkyl, —NH-aryl, —NH-heteroaryl, —NH-heterocycloalkyl, —NH—($C_1$-$C_4$alkyl)-heterocycloalkyl, —NH—($C_1$-$C_4$alkyl)-aryl, —NH—($C_1$-$C_4$alkyl)-heteroaryl, or —NH—($C_1$-$C_4$alkyl)-heterocycloalkyl comprising coupling a corresponding chloroprecursor compound of formula VII, as defined above, with the corresponding N-heterocycloalkyl compound or amine;

(iv) an Agent of the Invention of formula V in which $R_{13}$ is —$NH_2$, comprising reacting the corresponding methyl sulphinyl compound of formula VIII'

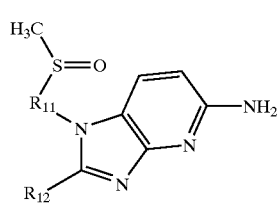

VIII' wherein $R_{11}$, and $R_{12}$ are as previously defined, with the corresponding amine of formula $R_{14}$—$NH_2$, and (v) an Agent of the Invention of formula V in which $R_{13}$ is piperazinyl, comprising reacting a corresponding methylsulphinyl compound of formula VIII''

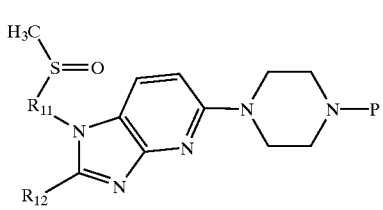

VIII'' wherein $R_{11}$ and $R_{12}$ are as previously defined and P is an N protecting group, with the corresponding amine of formula $R_{14}$—$NH_2$.

The synthesis of Agents of the Invention is further described in the following Examples.

EXAMPLES

Example 1

4-(4-Fluorophenyl)-2-(piperidin-4-yl)-5-(2-(1-(S)-phenylethyl)amino-4-pyrimidinyl)thiazole a) N-Ethoxycarbonylpiperidine-4-thiocarboxamide

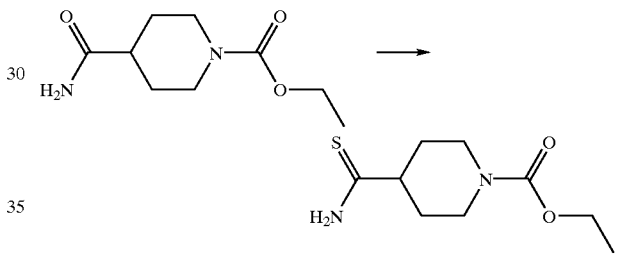

N-Ethoxycarbonylpiperidine-4-carboxamide (6 g 30 mmol) in toluene (300 ml) is treated with Lawesson's reagent (6.1 g 15 mmol) at room temperature for 18 h. The reaction mixture is evaporated and purified by $SiO_2$ chromatography (acetone/cyclohexane 20/80) to yield the title compound, which is recrystallised from hexanes (3.6 g 52.5%)

1H-NMR (400 MHz; $CDCl_3$): 1.28 (t, 3H); 1.72–1.83 (dq, 2H); 1.95 (d, 2H); 2.68–2.88 (m, 3H); 4.18 (q, 2H); 4.30 (bs, 2H); 6.92 (bs, 1H, NH); 7.51 (bs, 1H, NH) MS (m/z) CI: 217 (MH+, 50); 171 (100).

b) 4-Fluoro-2-(2-methylthio-4-pyrimidinyl)acetophenone

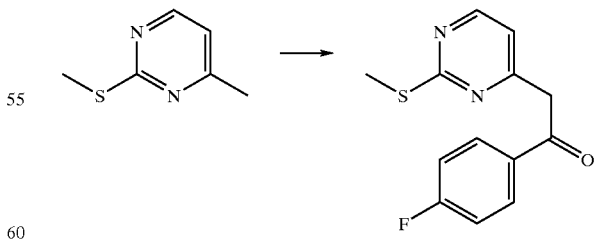

n-BuLi (10 ml of a 1.6 M solution in hexane; 12 mmol) is added at −78° C. to a solution of diisopropylamine (2.48 ml; 17 mmol) in THF (15 ml) and stirred for 5 min. 4-Methyl-2-(methylthio)pyrimidine (2 g; 14.5 mmol) dissolved in THF (2 ml) is added dropwise and stirred for 30 min at −78 C. 4-Fluoro-N-methoxy-N-methylbenzamide (2.66 g; 14.5 mmol) is dissolved in THF (3 ml) and added slowly to the reaction mixture. The mixture is warmed to r.t. within 45 min. and poured on water and extracted with ethyl acetate three times. The combined organic phases are dried over $Na_2SO_4$ and evaporated to dryness to yield 2.5 g (65%) of yellow crystals after recrystallisation from tert.butyl methyl ether/hexane.

1H-NMR (200 MHz $CDCl_3$): 3.00 (s, 3H); 6.30 (s, 1H; vinyl-H of enol); 7.00 (d, 1H); 7.50 (dd, 2H); 8.20 (dd, 2H); 8.7 (d, 2H). Due to pH-dependent keto-enol tautomery, signals may be duplicated.

c) 4-Fluoro-2-bromo-2-(2-methylthio-4-pyrimidinyl) acetophenone

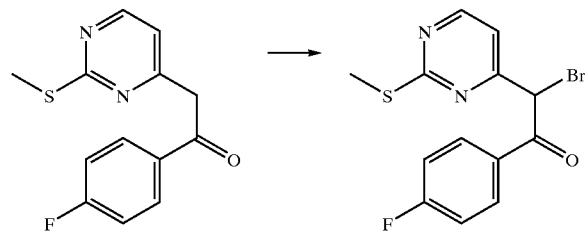

Bromine (1.22 g; 7.6 mmol) in acetic acid (5.6 ml) is added to a solution of 4-Fluoro-2-(2-methylthio-4-pyrimidinyl)acetophenone (2 g; 7.6 mmol) in acetic acid (40 ml). The initially thick precipitate is almost dissolved after 20 min., filtered and the filtrate evaporated to dryness. The residue is taken up in a saturated solution of $NaHCO_3$ and extracted three times with tert.butyl methyl ether. The combined organic phases are dried over $Na_2SO_4$ and evaporated to dryness to yield 2.6 g (100%) of a brown oil, which is used in the next step without purification.

d) 4-(4-Fluorophenyl)-2-(1-ethoxycarbonylpiperidin-4-yl)-5-(2-(methyhthio-4-pyrimidinyl)thiazole

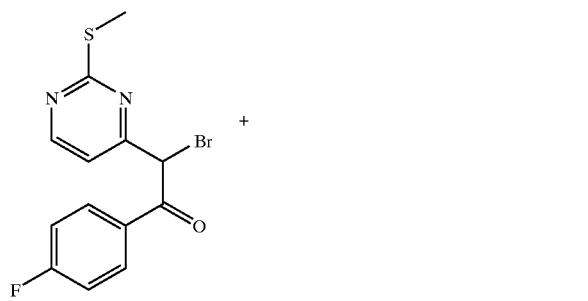

$Na_2SO_4$ (6.9 g 40 mmol) in DMF ($_{100}$ ml) is heated at 120° C. for 10 min. N-Ethoxycarbonylpiperidine-4-thiocarboxamide (8.6 g 40 mmol) is added as a solid and heating continued for 5 min. 2-Bromo-2-(2-methylthio-4-pyrimidinyl)-1-(4-fluorophenyl)ethanone (6.8 g 20 mmol) in DMF (20 ml) is rapidly added within 3 seconds and stirring continued at 120° C. for 10 min. The reaction mixture is poured on water and extracted with ethyl acetate three times. The combined organic phases are dried over $Na_2SO_4$, filtered, evaporated to dryness and purified by $SiO_2$ chromatography (ethyl acetate/hexanes 5/95 to 10/90) to yield the title compound as yellow crystals (2.2 g 24%)

1H-NMR (400 MHz; $CDCl_3$): 1.31 (t, 3H); 1.78–1.92 (dq, 2H); 2.21 (bd, 2H); 2.58 (s, 3H); 2.91–3.03 (bt, 2H); 3.18–3.28 (m, 1H); 4.20 (q, 2H); 4.25–4.40 (bs, 2H); 6.75 (d, 1H); 7.15 (t, 2H); 7.57 (dd, 2H); 8.31 (d, 1H).

MS (m/z) ESI: 459 (MH+,100).

e) 4-(4-Fluorophenyl)-2-(1-ethoxycarbonylpiperidin-4-yl)-5-(2-(methylsulfinyl-4-pyrimidinyl)thiazole

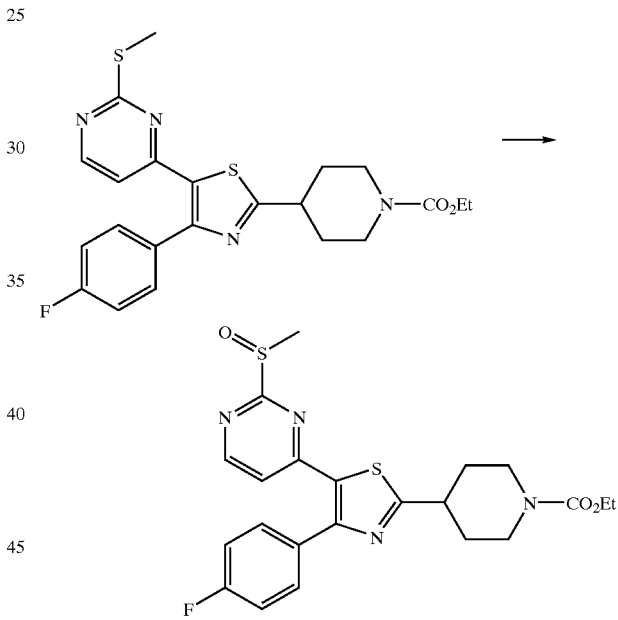

4-(4-Fluorophenyl)-2-(1-ethoxycarbonylpiperidin-4yl)-5-(2-(methylthio-4-pyrimidinyl)thiazole (4.0 g 8.7 mmol) in CH2Cl2 (80 ml) is treated with mCPBA (70% 2.1 g 8.7 mmol) at 0° C. for 15 min. The reaction mixture is poured on 2N $Na_2CO_3$ and extracted with $CH_2Cl_2$ three times. The combined organic phases were dried over Na2SO4, filtered, evaporated to dryness and purified by $SiO_2$ chromatography (acetone/hexanes 20/80 to 50/80) to yield the title compound (2.2 g 53%) as a white foam 1H-NMR (400 MHz; $CDCl_3$): 1.31 (t, 3H); 1.78–1.92 (dq, 2H); 2.21 (bd, 2H); 3.00 (s, 3H); 2.90–3.02 (m, 2H); 3.20–3.30 (bt, 1H); 4.18 (q, 2H); 4.25–4.40 (bs, 2H); 7.15 (d, 1H), 7.20 (t, 2H); 7.56 (dd, 2H); 8.63 (d, 1H).

MS (m/z) ESI: 475 (MH+).

f) 4-(4-Fluorophenyl)-2-(1-ethoxycarbonylpiperidin-4-yl)-5-(2-(1-(S)-phenylethyl)amino-4-pyrimidinyl)thiazole

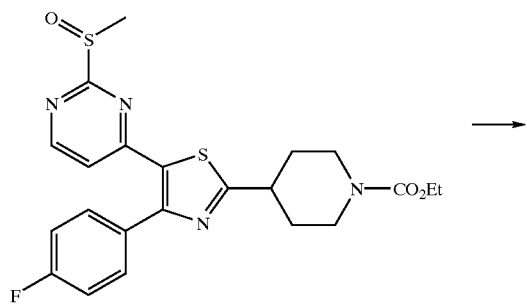

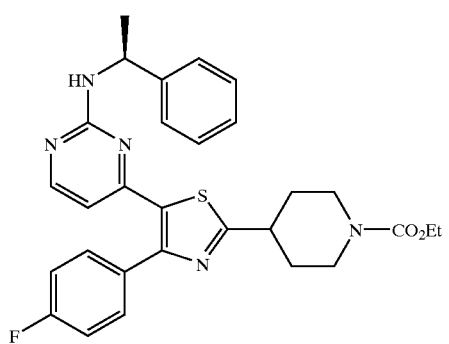

4-(4-Fluorophenyl)-2-(1-ethoxycarbonylpiperidin-4-yl)-5-(2-(methylsulfinyl-4-pyrimidinyl)thiazole (2.2 g 4.6 mmol) and 1-(S)-phenylethylamine (2.2 ml) are heated at 100° C. for 1 h. Purification over SiO$_2$ (acetone/cyclohexane 10/90 to 20/80) yielded the title compound as a pale yellow foam (2.4 g 95%).

$^1$H-NMR (400 MHz; CDCl$_3$): 1.31 (t, 3H); 1.51 (d, 3H); 1.75–1.88 (bq, 2H); 2.18 (bd 2H); 2.97 (bt, 2H); 3.20 (tt, 1H); 4.20 (q, 2H); 4.30 (bs, 2H); 5.17 (m, 1H); 5.46 (d, 1H, NH); 6.35 (d, 1H); 7.12 (t, 2H); 7.30–7.45 (m, 5H); 7.55 (dd, 2H); 8.08 (d, 1H).

MS (m/z) ESI: 523 (MH+, 100).

g) 4-(4Fluorophenyl)-2-(piperidin-4-yl)-5-(2-(1-(S)-phenylethyl)amino-4-pyrimidinyl)thiazole

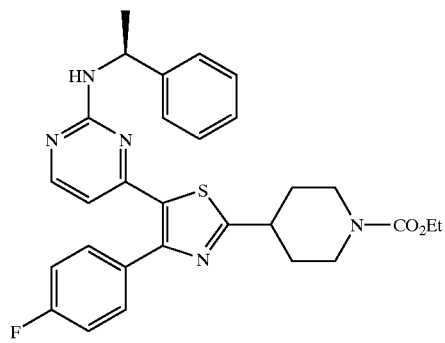

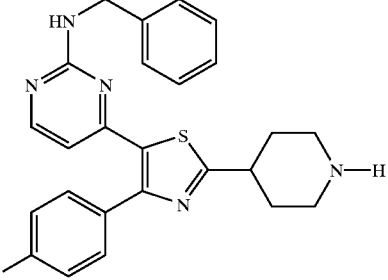

4-(4-Fluorophenyl)-2-(1-ethoxycarbonylpiperidin-4-yl)-5-(2-(1-(S)-phenylethyl)amino-4-pyrimidinyl)thiazole (2.4 g 4.5 mmol) was dissolved in CHCl$_3$ (45 ml) and treated with Me$_3$SiI (1.8 ml 13.5 mmol) at 60° C. for 6 h. The reaction mixture was combined with 6M HCl in propanol (18.5 ml), homogenized by vigorous stirring, poured on 2N NaOH and extracted twice with CH$_2$Cl$_2$. The combined organic phases were dried over Na$_2$SO$_4$, filtered, evaporated to dryness and purified by SiO$_2$ chromatography (tert.butyl methyl ether/MeOH/NH3conc. 95/4.5/0.5 to 80/18/2) to yield the title compound (1.8 g 87%) as a white foam.

1H-NMR (400 MHz; CDCl$_3$): 1.51 (d, 3H); 1.75–1.88 (bq, 2H); 2.18 (bd (2H); 2.82 (dt, 2H); 3.18 (tt, 1H); 3.25 (d, 2H); 5.17 (m, 1H); 5.45 (d, 1H, NH); 6.32 (d, 1H); 7.12 (t, 2H); 7.30–7.47 (m, 5H); 7.56 (dd, 2H); 8.07 (d, 1H).

MS (m/z) ESI: 460 (MH+, 100).

Example 2

4-(4-Fluorophenyl)-2-(1-methylpiperidin-4-yl)-5-(2-(1-(S)-phenylethyl)amino-4-pyrimidinyl)thiazole

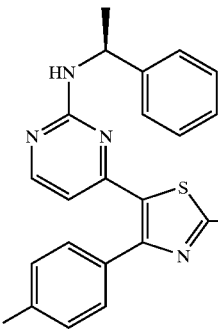

4-(4-Fluorophenyl)-2-(piperidin-4-yl-5-(2-(1-(S)-phenylethyl)amino-4-pyrimidinyl)thiazole (575 mg 1.25 mmol) is dissolved in MeOH (12 ml) and treated with an aqueous 36%-solution of formaldehyde (0.2 ml 2.5 mmol) and NaBH$_4$ (95 mg 2.5 mmol), which is added as a solid in 3 portions. After 30 min at room temperature the reaction mixture is poured on water and extracted three times with ethyl acetate. The combined organic phases are dried over Na$_2$SO$_4$, filtered, evaporated to dryness and purified by SiO$_2$ chromatography (tert.butyl methyl ether/MeOH/NH$_3$conc. 95/4.5/0.5 to 90/9/1) to yield the title compound (600 mg 85%) as pale yellow foam.

1H-NMR (400 MHz; CDCl$_3$): 1.51 (d, 3H); 1.88–2.01 (m, 2H); 2.08–2.25 (m, 4H); 2.48 (s, 3H); 2.97–3.08 (m, 3H); 5.18 (m, 1H); 5.48 (d, 1H, NH); 6.33 (d, 1H); 7.12 (t, 2H); 7.30–7.47 (m, 5H); 7.56 (dd, 2H); 8.05 (d, 1H).

MS (m/z) ESI: 474 (MH+, 100).

Example 3

4-(4-Fluorophenyl)-2-(piperidin-4-yl).5-(2-(1-(S)-phenylethyl)amino-4-pyridinyl)thiazole a) 4-Fluoro-2-(2-fluoropyridin-4-yl)acetophenone

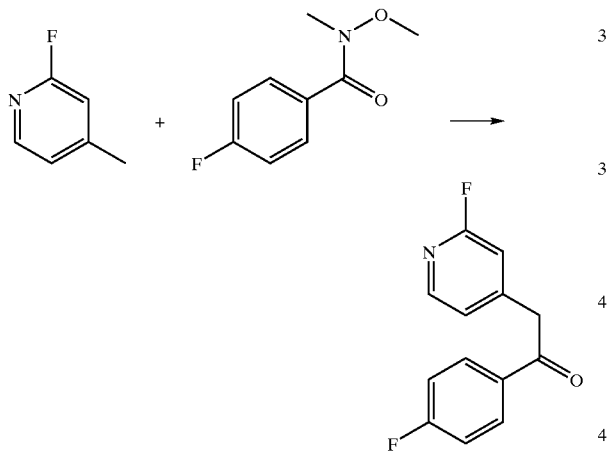

Diisopropylamine (0.93 ml; 6.55 mmol) in THF (6 ml) is cooled to −78 C. and treated with nBuLi (3.8 ml; 6.08 mmol of a 1.6 M solution in hexane). 2-Fluoro-4-methylpyridine (620 mg; 5.4 mmol) is added dropwise and stirred under argon for 30 min. 4-Fluoro-N-methoxy-N-methylbenzamide (1 g; 5.46 mmol) is added dropwise in THF (0.5 ml) and the reaction mixture allowed to warm up to room temperature within 10 min. then poured on a saturated solution of NaCl and extracted with TBME three times. The combined organic phases are washed with water, dried over Na$_2$SO$_4$, filtered and evaporated to dryness to yield the title compound as pale yellow crystals. Purification by recrystallisation from hot TBME rendered the desired compound as white solid (630 mg; 50%).

1H-NMR (200 MHz; CDCl$_3$): 4.35 (s, 2H); 6.88 (s, 1H); 7.08–7.30 (m, 3H); 7.99–8.15 (dd, 2H); 8.20 (d, 1H).

MS (e/z) ESI: 233 (M+, 5); 123 (100).

b) 4-Fluoro-2-bromo-(2-fluoropyridin-4-yl)acetophenone

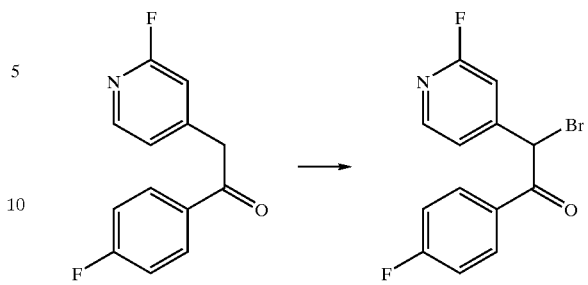

4-Fluoro-2-(2-fluoropyridin-4-yl)acetophenone (0.5 g; 2.1 mmol) dissolved in acetic acid (4 ml) is treated with bromine (0.34 g; 2.1 mmol) in acetic acid (1 ml) at room temperature for 2.5 h under stirring. The light brown solution is evaporated to dryness, dissolved in ether and extracted three times with diethyl ether. The combined organic phases are washed with a saturated solution of NaHCO$_3$, dried over Na$_2$SO$_4$, filtered and evaporated to dryness to yield the title compound as pale yellow oil (0.67 g; 100%).

1H-NMR (200 MHz; CDCl$_3$): 6.15 (s, 1H); 7.10–7.38 (m, 4H); 8.08 (dd, 2H); 8.23 (d, 1H).

MS (e/z) ESI: 232 (M-Br); 204 (10); 203 (12); 123 (100).

c) 4-(4-Fluorophenyl)-2-(1-ethoxycarbonylpiperidin-4-yl)-5-(2-fluoro-4-pyridinyl)thiazole

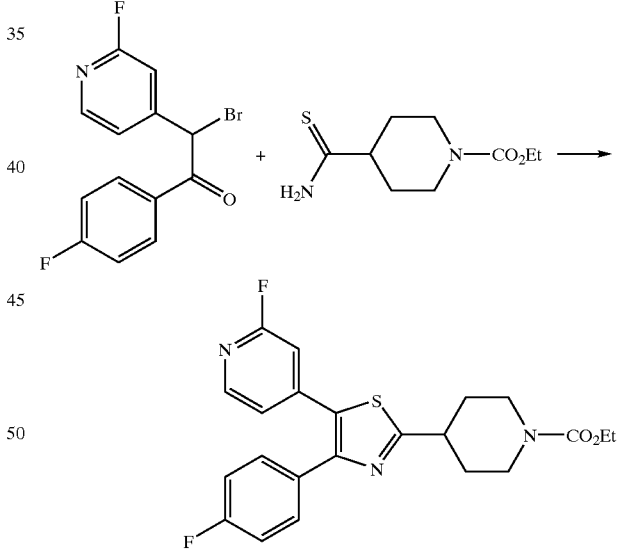

2-Bromo-2-(2-fluoro-4-pyridyl)-1-(4-fluorophenyl)ethanone (2.5 g 8.0 mmol) and N-ethoxycarbonyl-piperidine-4-thiocarboxamide (2.1 g 9.6 mmol) are heated at 60° C. in DMF (4 ml) for 30 min. The reaction mixture is poured on water and extracted with ethyl acetate three times. The combined organic phases are dried over Na$_2$SO$_4$, filtered, evaporated to dryness and purified by SiO$_2$ chromatography (ethyl acetate/cyclohexane 20/80 to 100/0) to yield the title compound as an oil (2.5 g 70%)

MS (m/z) ESI: 430 (MH+)

d) 4-(4-Fluorophenyl)-2-(1-ethoxycarbonylpiperidin-4-yl)-5-(2-(1-(S)-phenylethyl)amino-4-pyridinyl)thiazole

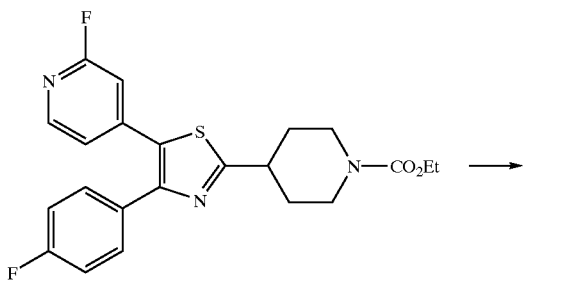

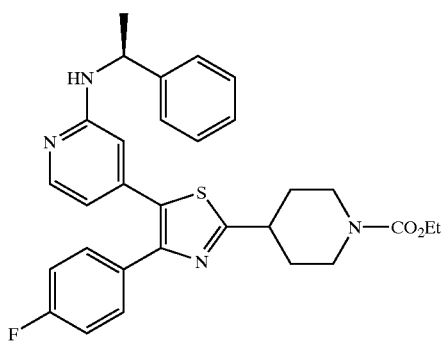

4-(4-Fluorophenyl)-2-(1-ethoxycarbonylpiperidin-4-yl)-5-(2-fluoro-4-pyridinyl)thiazole (2.4 g. 5.5 mmol) and 1-(S)-phenylethylamine (5.5 ml are heated to 195° C. for 5 h. The reaction mixture is evaporated and purified by SiO₂ chromatography (ethyl acetate/cyclohexane 20/80 to 30/70) to yield the title compound as a white foam (2.0 g 67.3%)

1H-NMR (400 MHz; CDCl₃): 1.31 (t, 3H); 1.55 (d, 3H); 1.72–1.87 (m, 2H); 2.17 (d, 2H); 2.98 (bt, 2H); 3.15–3.23 (m, 1H); 4.18 (q, 2H); 4.30 (bs, 2H); 4.56 (m, 1H); 5.01 (d, 1H, NH); 6.15 (s, 1H); 6.50 (d, 1H); 6.95 (dd, 2H); 7.22–7.46 (m, 5H); 7.45 (dd, 2H); 8.03 (d, 1H).

MS (m/z) CI: 531 (MH+, 100).

e) 4-(4Fluorophenyl)-2-(piperidin-4-yl)-5-(2(1-(S)-phenylethyl)amino-4-pyridinyl)thiazole

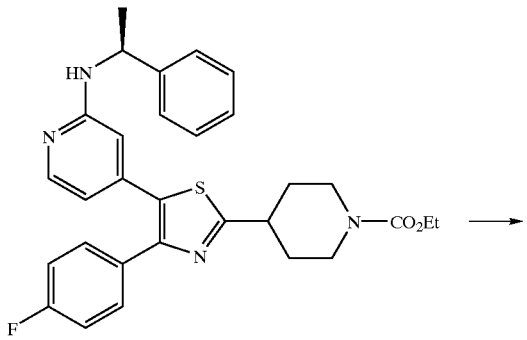

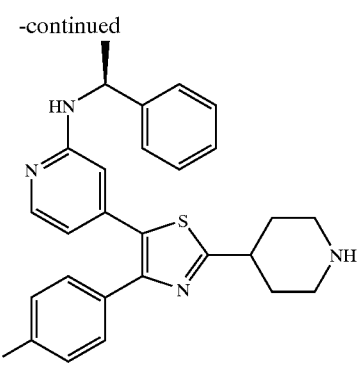

4-(4-Fluorophenyl)-2-(1-ethoxycarbonylpiperidin-4-yl)-5-(2-(1-(S)-phenylethyl)amino-4-pyridinyl)thiazole (2 g 3.7 mmol) is dissolved in CHCl₃ (37 ml) and treated with Me₃SiI (1.5 ml 11.1 mmol) at 60° C. for 5 h. A second portion of Me3SiI (0.75 ml 5.55 mmol ) was added and stirring continued for another 3 h at 60° C. The reaction mixture was combined with 6M HCl in propanol (15 ml), homogenized by vigorous stirring, poured on 2N NaOH and extracted twice with CH₂Cl₂. The combined organic phases were dried over Na₂SO₄, filtered, evaporated to dryness and purified by SiO₂ chromatography (tert.butyl methyl ether/MeOH/NH₃conc. 80/18/2) to yield the title compound (1.2 g 71%) as a white foam.

1H-NMR (400 MHz; CDCl₃): 1.53 (d, 3H); 1.77 (bs, 3H); 2.17 (bd, 2H); 2.78 (bt, 2H); (bt, 1H); 3.35 (bd, 2H); 4.55 (m, 1H); 5.00 (d, 1H, NH); 6.17 (s, 1H); 6.50 (d, 1H); 6.97 (bt, 2H); 7.20–7.37 (m, 5H); 7.45 (bt, 2H); 8.02 (d, 1H).

MS (m/z) CI: 459 (MH+)

Example 4

4-(4-Fluorophenyl)-2-(1-methylpiperidin-4-yl)-5-(2-(1-(S)-phenylethyl)amino-4-pyridinyl)thiazole

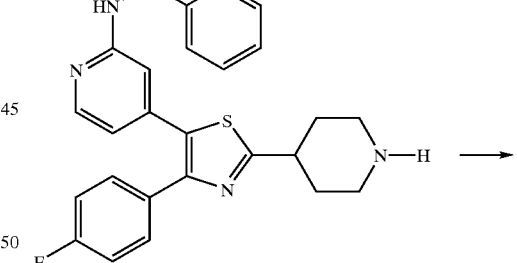

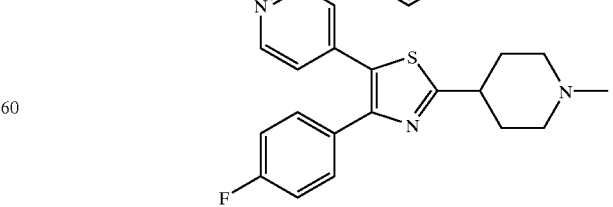

4-(4-Fluorophenyl)-2-(4-piperidinyl)-5-(2-(1-(S)-phenylethyl)-amino-4pyridinyl)thiazole (500 mg 1.09 mmol) is dissolved in MeOH (11 ml) and treated with an aqueous 36%-solution of formaldehyde (0.17 ml 2.18 mmol) and NaBH (83 mg 2.18 mmol), which is added as a solid in 3 portions. After 30 min at room temperature the reaction mixture is poured on water and extracted three times with ethyl acetate. The combined organic phases are dried over Na$_2$SO$_4$, filtered, evaporated to dryness and purified by SiO$_2$ chromatography (tert.butyl methyl ether/MeOH/NH$_3$conc. 95/4.5/0.5) to yield the title compound (550 mg 86%) as pale yellow foam 1H-NMR (400 MHz; CDCl$_3$): 1.53 (d, 3H); 1.83–1.98 (m, 2H); 2.07–2.20 (m, 4H); 2.35 (s, 3H); 2.98 (bd, 3H); 4.55 (m, 1H); 4.98 (d, 1H, NH); 6.15 (s, 1H); 6.50 (d, 1H); 6.98 (t, 2H); 7.22–7.35 (m, 5H); 7.45 (dd, 2H); 8.02 (d, 1H).

MS (m/z) ESI: 473 (MH+)

Example 5

2-(4-Fluorophenyl)-1-(2-cyclopentylamino-4-pyrimidinyl)-5-(piperidino-N-2-ethyl)imidazo-[4,5-b]pyridine a) 5-Chloro-2-(4-fluorophenyl)imidazo[4,5-b]pyridine

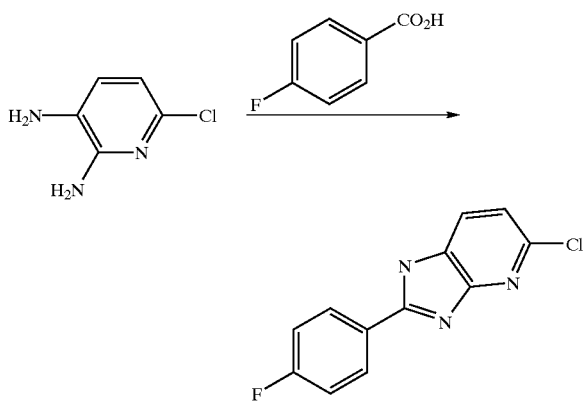

2,3-Diamino-6-chloropyridine (Davos-Bulk supplier, 2.25 g 15.6 mmol) and 4-fluorobenzoic acid (2.62 g 18.7 mmol) are treated with polyphosphoric acid (56.4 g) at 150° C. for 6 h. The reaction mixture is poured on ice-water/NH$_3$conc. and extracted with ethyl acetate three times. The combined organic phases are dried over Na$_2$SO$_4$, filtered and evaporated to dryness to yield the crude product, which is purified by recrystallisation from ethyl acetate/tert.butyl methyl ether to yield the title compound (1.8 g 44%) as grey crystals.

1H-NMR (400 MHz; DMSO-d6): 7.32 (d, 1H); 7.47 (t, 2H); 8.08 (bd, 1H); 8.28 (q, 2H); 13.6 (s, 1H).

MS (m/z) ESI: 247 (MH+; 100).

b) 5-Chloro-2-(4-fluorophenyl)-1-(2-methylthio-4-pyrimidinyl)imidazo[4,5-b]pyridine

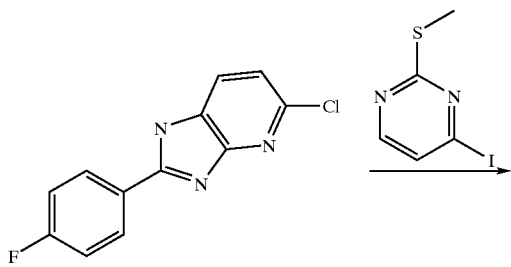

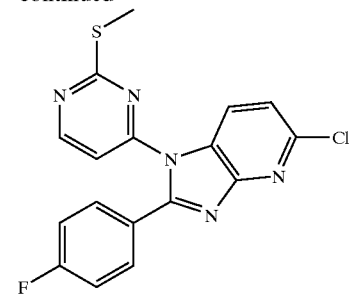

KN(TMS)$_2$ (1.42 g 7.16 mmol) in toluene (7 ml) is added at 0° C. to a solution of 5Chloro-2-(4fluorophenyl)imidazo [4,5-b]pyridine (1.9 g 6.66 mmol) in DMF (25 ml). After stirring 1 h at room temperature, 2-methylthio-4-iodopyrimidine (1.8 g 7.1 mmol) in toluene (7 ml) is added dropwise and heated for 20 h at 120° C. The reaction mixture is poured on water and extracted with ethyl acetate three times. The combined organic phases are dried over Na$_2$SO$_4$, filtered and evaporated to dryness to yield the crystalline crude product, which after recrystallisation from ethyl acetate yields the title compound as colorless crystals (1.76 g 67%).

1H-NMR (400 MHz; CDCl$_3$): 2.58 (s, 3H); 6.57 (d, 1H); 7.18 (t, 2H); 7.36 (d, 1H); 7.68 (q, 2H); 8.17 (d, 1H); 8.53 (d, 1H)

MS (m/z) ESI: 372 (MH+; 100); 352 (10); 336 (20).

The correct regiochemistry is demonstrated 2 steps later on the cyclopentylamine (d) analogue by ROESY.

c) 5-Chloro-2-(4-fluorophenyl)-1-(2-methylsulfinyl-4-pyrimidinyl)imidazo[4,5-b]pyridine

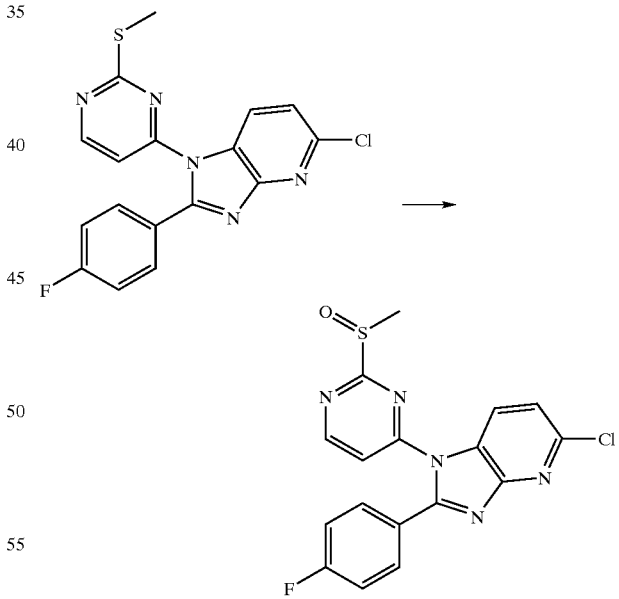

5-Chloro-2-(4-fluorophenyl)-1-(2-methylthio-4-pyrimidinyl)imidazo[4,5-b]pyridine (372 mg 1 mmol) is dissolved in CH$_2$Cl$_2$/HOAc (7 ml 5/2) and treated with MCPBA (270 mg 70% 1.1 mmol) at 0° C. for 30 min. The reaction mixture is poured on 2N Na$_2$CO$_3$ and extracted with ethyl acetate three times. The combined organic phases are dried over Na$_2$SO$_4$, filtered, evaporated to dryness and purified by SiO$_2$ chromatography (ethyl acetate) to yield the title compound (400 mg 100%) as yellow foam.

1H-NMR (400 MHz; CDCl₃): 3.08 (s, 3H); 6.92 (d, 1H); 7.25(t, 2H); 7.42 (d, 1H); 7.68 (q, 2H); 8.55 (d, 1H); 8.78 (bs, 1H).

MS (m/z) ESI: 388 (MH+, 100); 352 (30).

d) 5-Chloro-2-(4-fluorophenyl)-1-(2-cyclopentylamino-4-pyrimidinyl)imidazo[4,5-b]pyridine

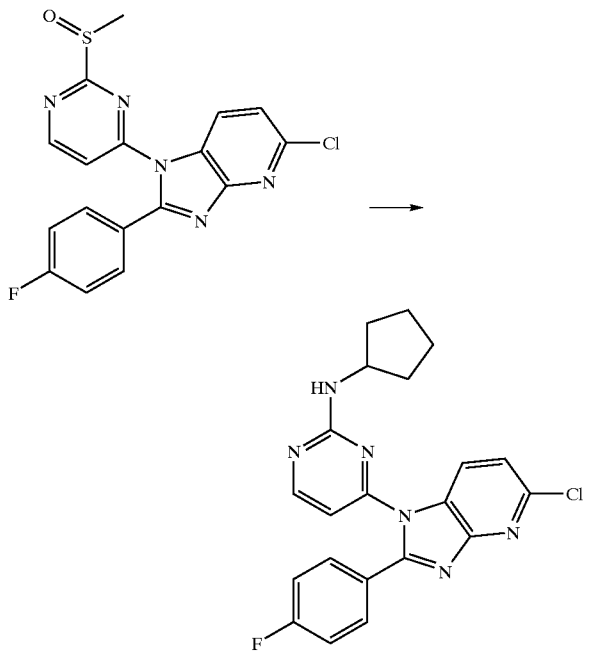

5-Chloro-2-(4-fluorophenyl)-1-(2-methylsulfinyl-4-pyrimidinyl)imidazo[4,5-b]pyridine (200 mg 0.52 mmol) and cyclopentylamine (1 ml) are heated to 80° C. for 1 h, evaporated and purified by SiO₂ chromatography (acetone/cyclohexane 10/90 to 20/80) to yield the title compound as white crystals (50 mg 24%).

1H-NMR (400 MHz; CDCl₃): 1.43–1.86 (m, 6H); 1.95–2.20 (bs, 2H); 4.08–4.42 (bs, 1H); 5.30–5.52 (bs, 1H, NH); 6.20 (bs, 1H); 7.17 (t, 2H); 7.33 (d, 1H); 7.71 (q, 2H); 8.10 (d, 1H); 8.28 (d, 1H. The correct regiochemistry is demonstrated by ROESY.

MS (m/z) ESI: 409 (MH+, 100)

e) 2-(4-Fluorophenyl)-1-(2-cyclopentylamino-4-pyrimidinyl)-5-vinylimidazo[4,5-b]pyridine

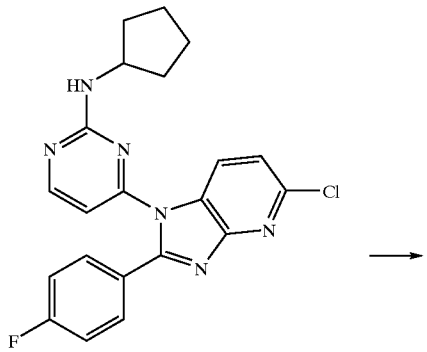

-continued

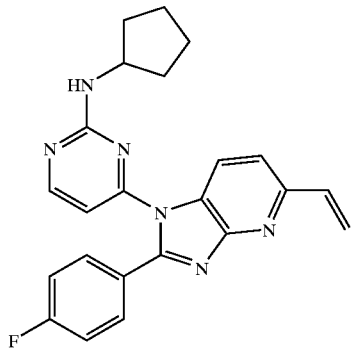

2-(4-Fluorophenyl)-1-(2-cyclopentylamino-4-pyrimidinyl)-5-chloroimidazo[4,5-b]pyridine (50 mg 0.12 mmol), vinyltributylstannane (4.3 ml 0.15 mmol) and PdCl₂(PPh₃)₂ (8.6 mg 0.01 mmol) are dissolved in xylene (1 ml) and heated to 160° C. for 1 h under argon. The reaction mixture is purified over SiO₂ (acetone/hexanes 15/85) to yield the title compound as colorless crystals (42 mg 86%)

1H-NMR (400 MHz; CDCl₃): 1.45–1.86 (m, 6H); 1.93–2.20 (bs, 2H); 4.06–4.48 (bs, 1H); 5.35 (bs, 1H, NH); 5.53 (d, 1H); 6.21 (bs, 1H); 6.44 (d, 1H); 6.95 (q, 1H); 7.18 (t, 2H); 7.48 (d, 1H); 7.73 (q, 2H); 8.08 (d, 1H); 8.30 (d, 1H).

MS (m/z) ESI: 399 (M-H).

f) 2-(4-Fluorophenyl)-1-(2-cyclopentylamino-4-pyrimidinyl)-5-(piperidino-N-2-ethyl)imidazo-[4,5-b]pyridine

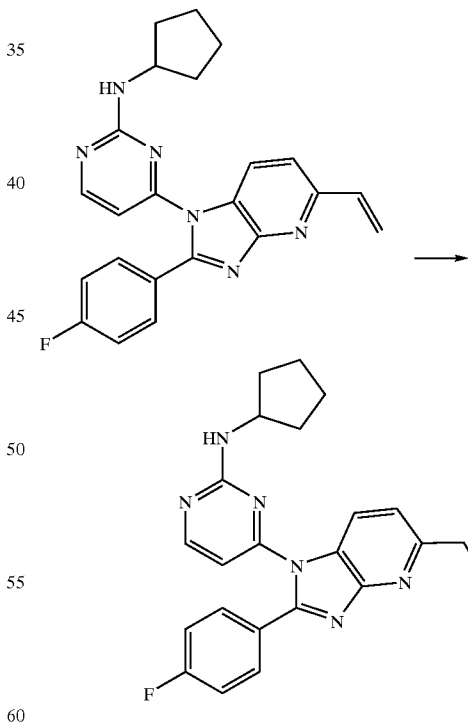

2-(4-Fluorophenyl)-1-(2-cyclopentylamino-4-pyrimidinyl)-5-vinylimidazo[4,5-b]pyridine (50 mg 0.13 mmol ) and piperidine (0.3 ml 3 mmol) are refluxed in HOAc (1 ml) for 1.5 h, poured on a saturated solution of Na₂CO₃ and extracted with ethyl acetate three times. The combined organic phases are dried over Na₂SO₄, filtered, evaporated to dryness and purified by SiO₂ chromatography (tert.butyl methyl ether/MeOH/NH₃conc. 85/15/1) to yield the title compound (60 mg 98%) as yellow crystals.

1H-NMR (400 MHz; DMSO, 120° C.): 1.40–1.90 (m, 14H); 2.55 (bs, 2H); 2.75–2.91 (m, 4H); 3.08 (t, 2H); 4.03 (m, 1H); 6.43 (d, 1H); 6.97 (bs, 1H, NH); 7.28 (t, 3H); 7.69 (dd, 2H) 8.00 (d, 1H); 8.38 (d, 1H).

MS (m/z) ESI: 486 (MH+; 100)

Example 6

2-(4-Fluorophenyl)-1-(2-cyclopentylamino-4-pyrimidinyl)-5-(N,N-diethyl-amino-N-2-ethyl)imidazo[4,5-b]pyridine

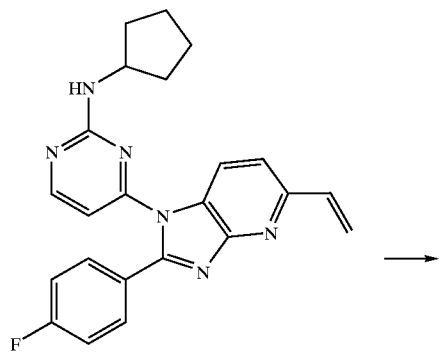

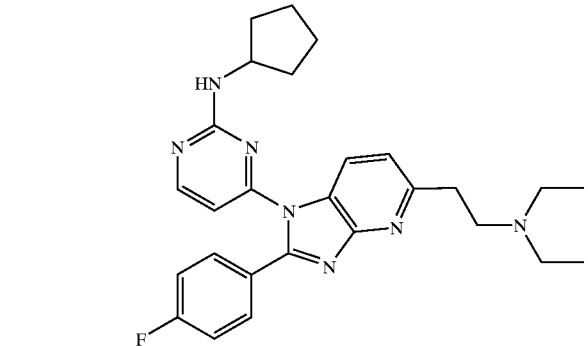

The crystalline title compound (48 mg 50%) is prepared by analogy to the previous example.

1H-NMR (400 MHz; CDCl₃): 1.12 (bt, 6H); 1.46–2.20 (m, 8H); 2.71 (bd, 4H); 2.97–3.20 (bd, 4H); 4.05–4.38 (bs, 1H); 5.35 (bs, 1H, NH); 6.18 (bs, 1H); 7.12(t, 2H); 7.20 (d, 1H); 7.71 (dd, 2H); 8.03 (d, 1H); 8.29 (d, 1H).

MS (m/z) ESI: 474 (MH+, 100).

Example 7

2-(4-Fluorophenyl)-1-(2-cyclopentylamino-4-pyrimidinyl)-5-(morpholino-N-2-ethyl)imidazo[4,5-b]pyridine

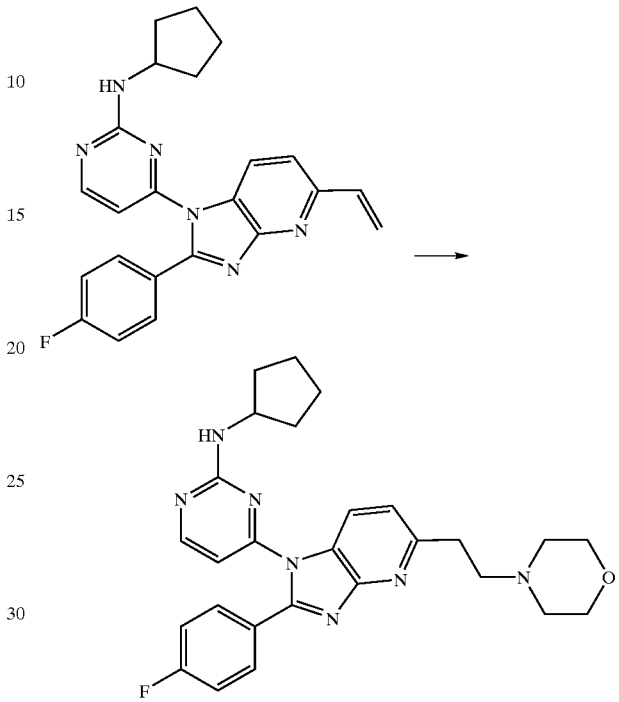

The crystalline title compound (78 mg 66%) is prepared by analogy to the previous example.

1H-NMR (400 MHz; CDCl₃): 1.45–1.85 (m, 6H); 1.93–2.13 (bs, 2H); 2.59 (bs, 4H); 2.95 (t, 2H); 3.18 (t, 2H); 3.78 (t, 4H); 4.03–4.41 (bs, 1H); 5.35 (bs, 1H, NH); 6.20 (bs, 1H); 7.15 (t, 2H); 7.20 (d, 1H); 7.72 (dd, 2H); 8.05 (d, 1H); 8.30 (d, 1H).

MS (nz) ESI: 488 (MH+, 100);

Example 8

2-(4-Fluorophenyl)-1-(2-cyclopentylamino-4pyrimidinyl)-5-(isopropylamino-N-2-ethyl)imidazo[4,5-b]pyridine

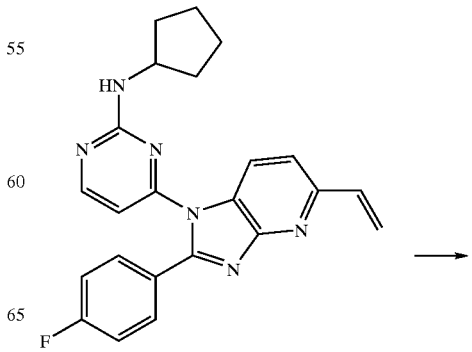

-continued

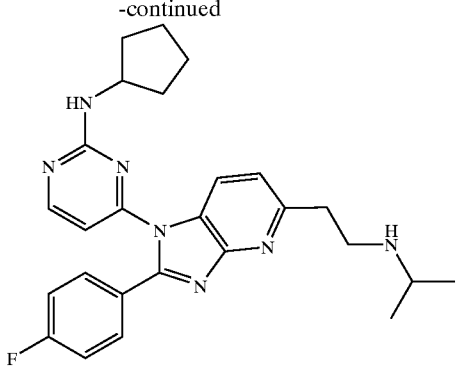

The crystalline title compound (30 mg 33%) is prepared by analogy to the previous example.

1H-NMR (400 MHz; CDCl$_3$): 1.15 (d, 6H); 1.45–2.15 (m, 8H); 2.95 (m, 1H); 3.21 (s, 4H); 4.08–4.35 (bs, 1H); 5.38 (bs, 1H, NH); 6.20 (bs, 1H); 7.16 (t, 2H); 7.22 (d, 1H); 7.73 (dd, 2H); 8.05 (d, 2H); 8.29 (d, 1H).

MS (m/z) ESI: 460 (MH+, 100).

Example 9

2-(4-Fluorophenyl)-1-(2-cyclopentylamino-4-pyrimidinyl)-5-(pyrrolidino-N-2-ethyl)imidazo[4,5-b]pyridine

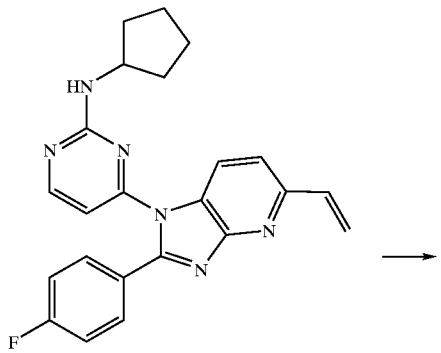

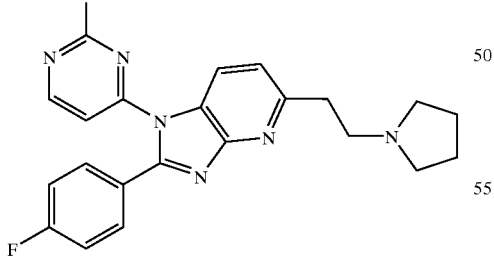

The crystalline title compound (34 mg 36%) is prepared by analogy to the previous example.

1H-NMR (400 MHz; CDCl$_3$): 1.45–2.18 (m, 12H); 2.65 (bs, 4H); 3.03 (m, 2H); 3.23 (m, 2H); 4.20 (bs, 1H); 5.35 (bs 1H, NH); 6.18 (bs, 1H); 7.14 (t, 2H); 7.22 (d, 1H); 7.74 (dd, 2H); 8.04 (d, 1H); 8.28 (d, 1H).

MS (m/z) ESI: 472 (MH+, 100).

Example 10

2-(4-Fluorophenyl)-1-(2-cyclopentylamino-4-pyrimidinyl)-5-(3-pyridyl)imidazo-[4,5-b]pyridine

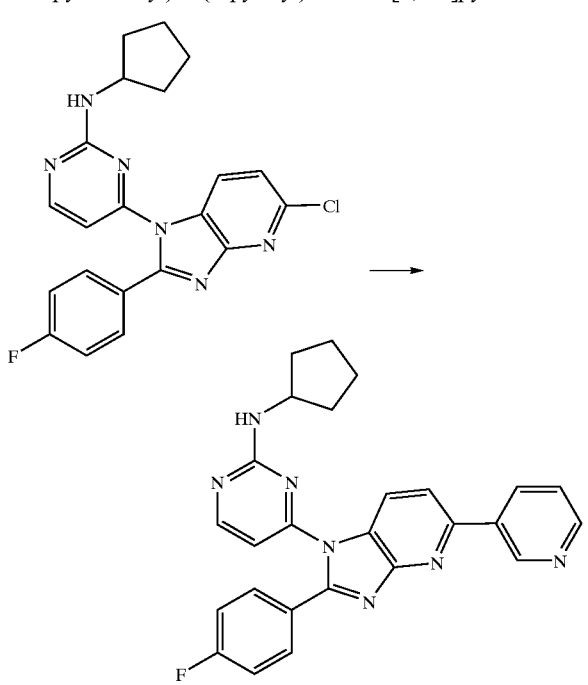

5-Chloro-2-(4-fluorophenyl)-1-(2-cyclopentylamino-4-pyrimidinyl)imidazo[4,5-b]pyridine (2 g 4.9 mmol), 3-tributylstannylpyridine (3.6 g 9.8 mmol) and PdCl$_2$(PPh$_3$)$_2$ (340 mg 0.48 mmol) are heated in xylene (50 ml) for 3 h at 150° C. under argon. The reaction mixture is filtered at 60° C. and chromatographed over SiO$_2$ (acetone/hexanes 3/7 to 6/4) to yield pale yellow crystals (1.3 g). Recrystallisation from THF/hexanes renders the title compound as colorless crystals (985 mg 45%).

1H-NMR (400 MHz; CDCl$_3$): 1.45–1.90 (m, 6H); 1.95–2.20 (bs, 2H); 4.08–4.45 (bs, 1H); 5.41 (bs, 1H, NH); 6.25 (bs, 1H); 7.18 (t, 2H); 7.48 (m, 1H); 7.78 (dd, 2H); 7.86 (d, 1H); 8.25 (d, 1H); 8.33 (d, 1H); 8.60 (d, 1H); 8.68 (d, 1H).9.38 (s, 1H).

MS (m/z) ESI: 450 (M-H).

Example 11

2-(4Fluorophenyl-1-(2-cylopentylamino-4-pyrimidinyl)-5-(4-pyridyl)imidazo[4,5-b]pyridine

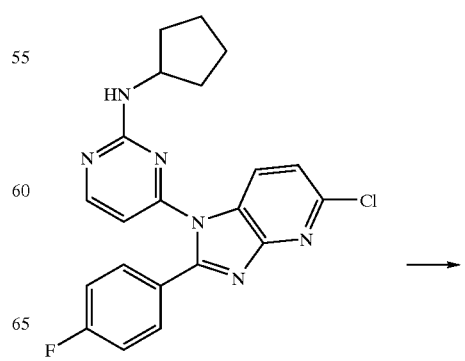

-continued

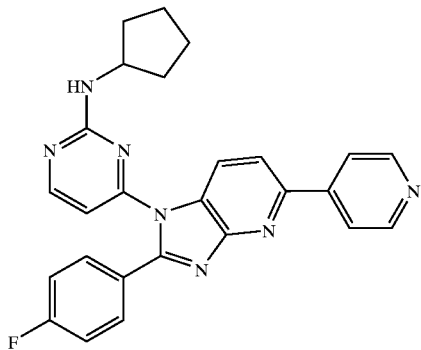

The white crystalline title compound (1.3 g 70%) is obtained by analogy to the previous example with the exception that 4-trimethylstannylpyridine was used in the coupling reaction.

1H-NMR (400 MHz; CDCl$_3$): 1.45–1.90 (m, 6H); 1.95–2.20 (bs, 2H); 4.08–4.45 (bs, 1H); 5.41 (bs, 1H, NH); 6.25 (bs, 1H); 7.18 (t, 2H); 7.78 (dd, 2H); 7.88 (d, 1H); 8.12 (d, 2H); 8.28 (d, 1H); 8.33 (d, 1H); 8.80 (d, 2H).

MS (m/z) ESI: 452.3 (MH+, 100).

Example 12

2-(4-Fluorophenyl)-1-(2-(1-(S)-phenylethyl)amino-4-pyrimidinyl)-5-aminoimidazo[4,5-b]pyridine a) 2-(4-Fluorophenyl)-5-aminoimidazo[4,5-b]pyridine

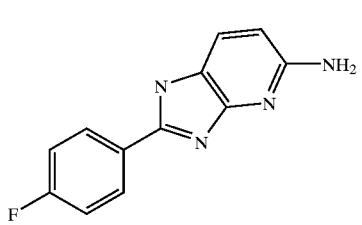

2,3,6-Triaminopyridine (Austin Products; 372 mg 3 mmol) and 4-fluorobenzoic acid (420 mg 3 mmol) are treated with polyphosphoric acid (30 g) at 150° C. for 1 h. The reaction mixture is poured on ice-water/NH$_3$conc. and extracted with ethyl acetate three times. The combined organic phases are dried over Na$_2$SO$_4$, filtered and evaporated to dryness to yield the crude product, which is purified by SiO$_2$ chromatography (acetone/cyclohexane 20/80 to 50/80) and rendered the title compound as pale yellow crystals (200 mg 29%)

1H-NMR (400 MHz; DMSO): 5.92 (bs, 2H, NH2); 6.40 (d, 1H); 7.35 (t, 2H); 7.65 (d, 1H) 8.13 (dd, 2H); 12.80 (bs, 1H, NH).

MS (n/z) ESI: 229 (MH+, 100).

b) 2-(4-Fluorophenyl)-1-(2-methylthio-4-pyrimidinyl)-5-aminoimidazo[4,5-b]pyridine

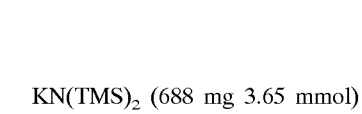

KN(TMS)$_2$ (688 mg 3.65 mmol) in toluene (3.5 ml) is added at 0° C. to a solution of 2-(4-fluorophenyl)-5-aminoimidazo[4,5-b]pyridine (684 mg 3 mmol) in DMF (10 ml). After stirring 1 h at room temperature, 2-methylthio4-iodopyrimidine (832 mg 3.3 mmol) in toluene (3.3 ml) is added dropwise and heated for 18 h at 120° C. The reaction mixture is poured on water and extracted with ethyl acetate three times. The combined organic phases are dried over Na$_2$SO$_4$, filtered and evaporated to dryness to yield the crude product, which is purified by SiO$_2$ chromatography (acetone/cyclohexane 20/80 to 60/40) and renders the title compound as a yellow foam (300 mg 27%)

1H-NMR (400 MHz; CDCl$_3$): 2.58 (s, 3H); 4.60 (bs, 2H, NH2); 6.55 (d, 1H); 6.59 (d, 1H); 7.16 (t, 2H); 7.63 (dd, 2H); 8.00 (d, 1H); 8.48 (d, 1H). The correct regiochemistry was demonstrated by ROESY.

MS (m/z) ESI: 353 (MH+, 100).

c) 2-(4-Fluorophenyl)-1-(2-(1-(S)-phenylethyl)amino-4-primidinyl)-5-aminoimidazo[4,5-b]pyridine

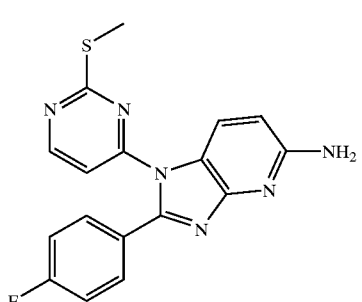

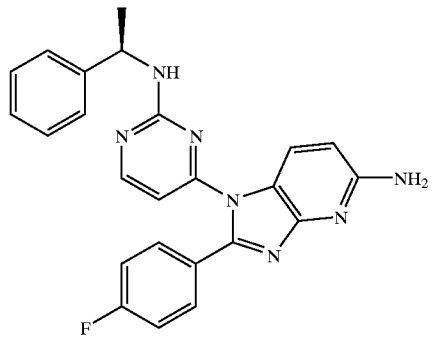

2-(4-Fluorophenyl)-1-(2-methylthio-4-pyrimidinyl)-5-aminoimidazo[4,5-b]pyridine (110 mg, 0.31 mmol) is dissolved in CH$_2$Cl$_2$/HOAc 1:1 (6.2 ml), combined at 0° C. with mCPBA (84 mg 70% 0.34 mmol) and stirred for 30 min. The reaction mixture is poured on 2N Na$_2$CO$_3$ and extracted with ethyl acetate three times. The combined organic phases are dried over Na$_2$SO$_4$, filtered and evaporated to dryness to yield the crude sulfoxide (110 mg). 50 mg are dissolved in 1-(S)-phenylethylamine (0.5 ml) and heated to 120° C. for 1 h. Purification over RP18 (CH$_3$CN/Water 70/30 to 10/90) yielded the title compound as light brown foam (30 mg 52%)

1H-NMR (400 MHz; CDCl$_3$): 1.60 (d, 3H); 4.50 (bs, 2H, NH2); 5.10 (bs, 1H); 5.78 (bs, 1H); 6.08 (d, 1H); 6.25 (bs, 1H); 7.11 (t, 2H); 7.37 (m, 1H); 7.41 (m, 5H); 7.63 (dd, 2H); 8.22 (d, 1H).

MS (m/z) El: 425 (M+, 70); 410 (40).

Example 13

2-(4-Fluorophenyl)-1-(2-cyclopentylamino-4-pyrimidinyl)-5-aminoimidazo[4,5b]pyridine

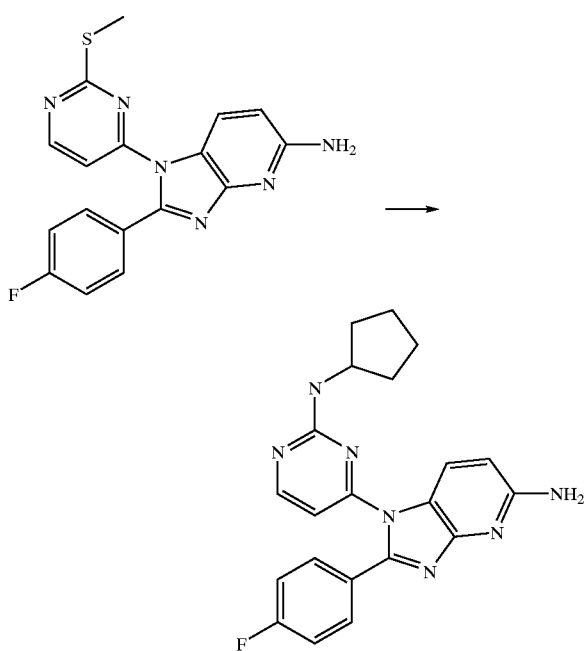

The title compound is prepared from the sulfoxide (60 mg 0.16 mmol) in the above procedure and cyclopentylamine (0.8 ml) by heating to 120° C. for 1 h and purifying over RP18 (CH$_3$CN/Water 70/30 to 10/90). The title compound is obtained as a yellow powder (30 mg 44%)

1H-NMR (400 MHz; CDCl$_3$): 1.47–2.15 (m, 8H); 4.20 (bs, 1H); 4.55 (s, 2H; NH2); 5.34 (bs, 1H); 6.15 (s, 1H, NH); 6.54 (d, 1H); 7.12 (t, 2H); 7.68 (dd, 2H); 7.93 (d, 1H); 8.25 (d, 1H).

MS (m/z) EI: 389 (M+, 100).

Example 14

2-(4-Fluorophenyl)-1-(2-(1-(S)-phenylethyl)amino-4-pyrimidinyl)-5-(4-NH-1-piperazinyl)imidazo[4,5-b]pyridine a) 5-Nitro-6-amino-2-(4-ethoxycarbonyl-1-piperazinyl)pyridine

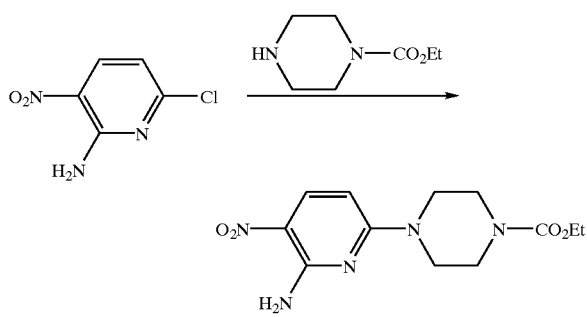

6-Amino-2-chloro-5-nitropyridine (Acros, 3.66 g 21 mmol) and 1-ethoxycarbonylpiperazine (6.36 g 42 mmol) in isopropanol (85 ml) are refluxed for 3 h. The reaction mixture with a yellow precipitate is poured on water/Na$_2$CO$_3$ and extracted twice with methylene chloride. The combined organic phases are dried over Na$_2$SO$_4$, filtered and evaporated to dryness to yield the title compound as yellow crystals, which are purified by recrystallisation from tert.-butyl methyl ether (5.5 g 89%).

1H-NMR (400 MHz; CDCl$_3$): 1.23 (t, 3H); 3.51 (m, 4H); 3.66 (m, 4H); 4.12 (q, 2H); 2H); (d, 1H); 8.15 (d, 1H).

MS (m/z) EI: 295 (M+, 60); 193 (50); 167 (100).

b) 5,6Diamino-2-(4-ethoxycarbonyl-1-piperazinyl)pyridine

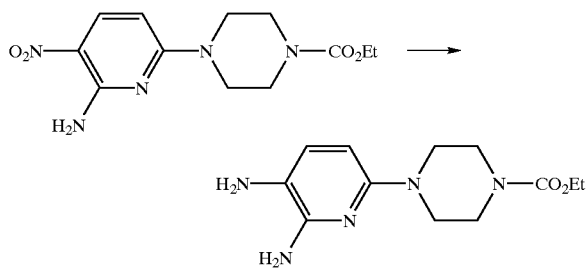

5-Nitro-6-amino-2-(4-ethoxycarbonyl-1-piperazinyl)pyridine (4.5 g 15.2 mmol) in EtOH (200 ml) is hydrogenated at 1 atm over 10% Pd/C (1.5 g), filtered after hydrogen uptake was complete (2.5 h), combined with 4-fluorobenzoic acid (2.13 g 15.2 mmol) in EtOH (50 ml), evaporated to dryness and used without further purification in the following step.

c) 2-(4-Fluorophenyl)-5-(4-NH-1piperazinyl)imidazo[4,5-b]pyridine

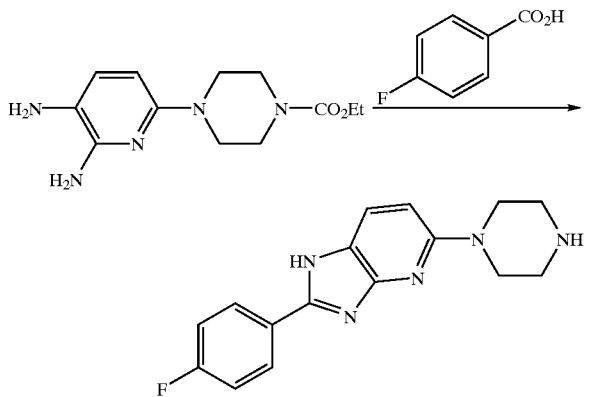

The mixture of 5,6-Diamino-2-(4-ethoxycarbonyl-1-piperazinyl)pyridine from the previous hydrogenation (4.5 g, 15.2 mmol) and 4-fluorobenzoic acid (2.13 g 15.2 mmol) is treated with polyphosphoric acid (76 g) at 150° C. for 1 h 15 min. The reaction mixture is poured on ice-water/ $Na_2CO_3$ and extracted with ethyl acetate three times. The combined organic phases are dried over $Na_2SO_4$, filtered and evaporated to dryness to yield the title compound as brownish crystals (1.6 g, 35%).

1H-NMR (400 MHz; DMSO): 2.73 (m, 4H); 3.43 (m, 4H); 6.78 (d, 1H); 7.35 (t, 2H); 7.80 (d, 1H); 8.18 (dd, 2H).

MS (m/z) CI:298 (MH+, 100); 278 (20).

d) 2-(4-Fluorophenyl)-5-(4-tert.butoxycarbonyl-1-piperazinyl)imidazo[4,5-b]pyridine

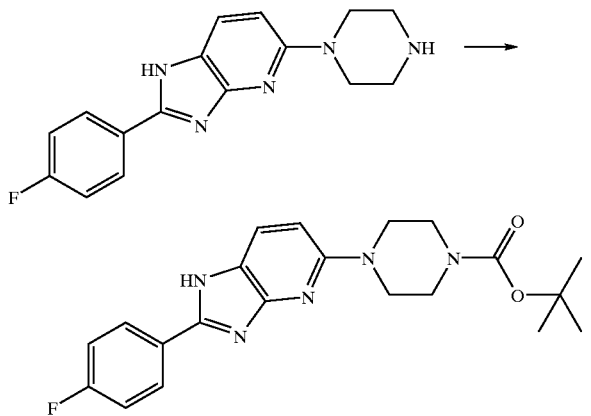

2-(4-Fluorophenyl)-5-(4-NH-1-piperazinyl)imidazo[4,5-b]pyridine (1.57 g, 5.3 mmol) in THF (53 ml) is treated with $(BOC)_2O$ (1.27 g, 5.83 mmol) for 30 min. at room temperature, poured on water and extracted with ethyl acetate three times. The combined organic phases are washed with brine, dried over $Na_2SO_4$, filtered and evaporated to dryness. Purification over $SiO_2$ (acetone/hexanes 10/80 to 50/50) yields the title compound (1.6 g, 74.5%) as brownish crystals.

1H-NMR (400 MHz; CDCl$_3$): 1.52 (s, 9H); 3.52–3.73 (bs, 8H); 6.71 (d, 1H); 7.18 (t, 2H); 7.93 (bs, 1H); 8.07 (bt, 2H), 10.70 (bs, 1H, NH).

MS (m/z) EI: 397 (M+, 100); 341 (90); 241 (100).

e) 2-(4-Fluorophenyl)-1-(2-methylthio-4-pyrimidinyl)-5-(4-tert.butoxycarbonyl-1-piperazinyl)imidazo[4,5-b]pyridine

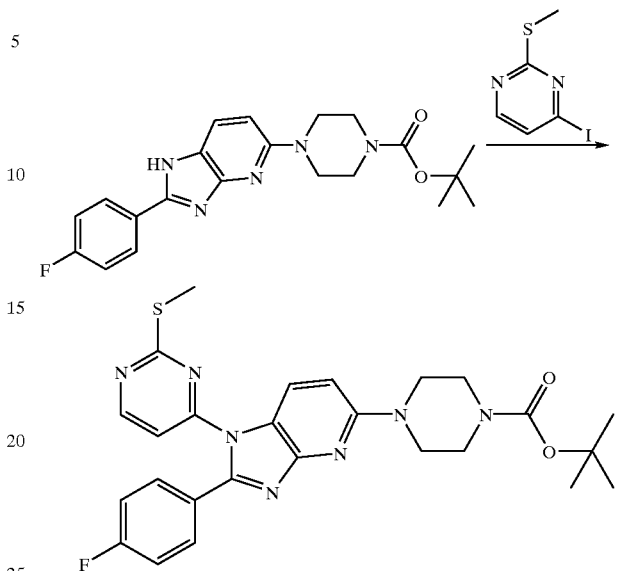

KN(TMS)$_2$ (812 mg, 3.85 mmol) in toluene (3.85 ml) is added at 0° C. to a solution of 2-(4-Fluorophenyl)-5-(4-tert.butoxycarbonyl-1-piperazinyl)imidazo[4,5-b]pyridine (1.4 g, 3.5 mmol) in DMF (7 ml). After stirring at room temperature for 30 min., 4-iodo-2-methylthiopyrimidine (970 mg, 3.85 mmol) in toluene (3.85 ml) is added and the reaction stirred at room temperature for 1 h. Toluene is evaporated, the reaction mixture heated to 120° C. for 18 h, poured on water and extracted with ethyl acetate (containing 5% EtOH) three times. The combined organic phases are washed with brine, dried over $Na_2SO_4$, filtered and evaporated to dryness. Purification over $SiO_2$ (acetone/hexanes 20/80) renders the title compound (950 mg, 52%) as colorless foam.

1H-NMR (400 MHz; CDCl$_3$): 1.51 (s, 9H); 2.55 (s, 3H); 3.61 (m, 4H); 3.69 (m, 4H); 6.55 (d, 1H); 6.77 (d, 1H); 7.15 (t, 2H); 7.65 (dd, 2H); 8.06 (d, 1H); 8.47 (d, 1H). The correct regiochemistry was demonstrated by ROESY.

MS (m/z) ESI: 522 (MH+, 100).

f) 2-(4-Fluorophenyl)-1-(2-(1-(S)-phenylethyl)amino-4-pyrimidinyl)-5-(4-tert.butoxycarbonyl-1-piperazinyl)imidazo[4,5-b]pyridine

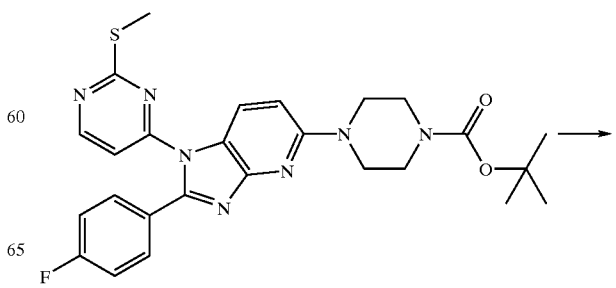

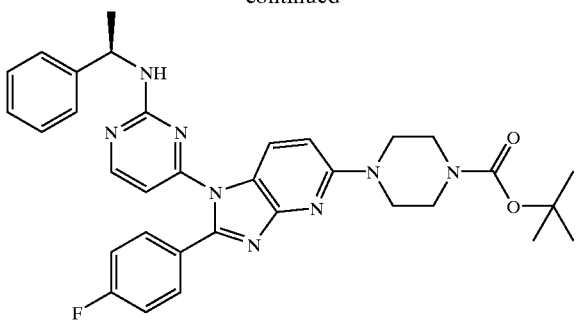

2-(4-Fluorophenyl)-1-(2-methylthio-4-pyrimidinyl)-5-(4-tert.butoxycarbonyl-1-piperazinyl)imidazo[4,5-b]pyridine (106 mg, 0.2 mmol) is dissolved in $CH_2Cl_2$/HOAc 1:1 (10 ml), combined with mCPBA (113 mg 70%, 0.24 mmol) and stirred for 15 min. The reaction mixture is poured on water and extracted with $CH_2Cl_2$ three times. The combined organic phases are dried over $Na_2SO_4$. filtered and evaporated to dryness to yield the crude sulfoxide (100 mg), which is dissolved in 1-(S)-phenylethylamine (0.2 ml) and heated to 120° C. for 1 h. Purification over $SiO_2$ (acetone/hexanes 1:1) yielded the title compound as colorless foam (45 mg 35%)

1H-NMR (400 MHz; $CDCl_3$): 1.51 (s, 9H); 1.62 (d, 3H); 3.58–3.67 (m, 8H); 5.10 (bs, 1H); 5.75 (bs, 1H); 6.08 (d, 1H); 6.45 (bs 1H, NH); 7.11 (t, 2H); 7.33–7.43 (m, 6H); 7.65 (dd, 2H); 8.22 (d, 1H).

MS (m/z) ESI: 595 (MH+, 100).

g) 2-(4-Fluorophenyl)-1-(2-(1-(S)-phenylethyl)amino-4-pyrimidinyl)-5-(4-NH-1-piperazinyl)imidazo[4,5-b]pyridine

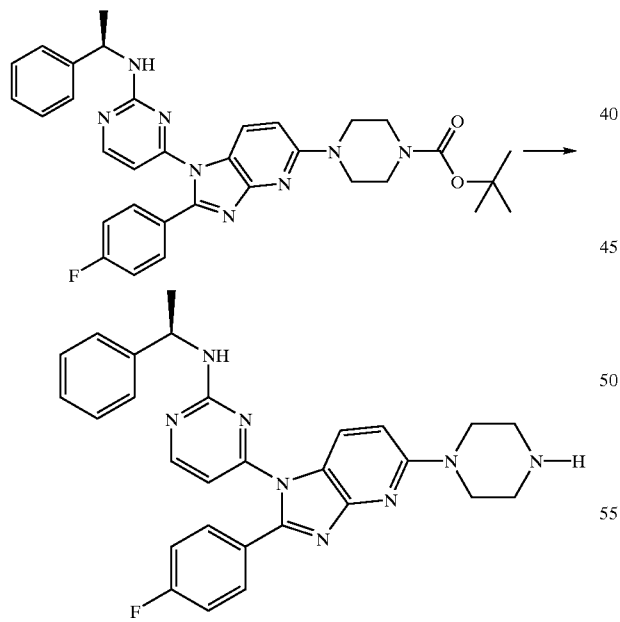

2-(4-Fluorophenyl)-1-(2-(1-(S)-phenylethyl)amino-4-pyrimidinyl)-5-(4-tert.butoxycarbonyl-1-piperazinyl)imidazo[4,5-b]pyridine (280 mg, 0.67 mmol) is dissolved in EtOH/HClconc 1/1 (9.4 ml) and stirred at room temperature for 30 min. The reaction mixture is poured on a saturated solution of $Na_2CO_3$ and extracted with ethyl acetate three times. The combined organic phases are dried over $Na_2SO_4$, filtered and evaporated to dryness. Purification over $SiO_2$ (tert.-butyl methyl ether/MeOH/$NH_3$conc 90/9/1) yields the title compound as a yellow foam (200 mg, 86%)

1H-NMR (400 MHz; $CDCl_3$): 1.61 (d, 3H); 1.89 (bs, 1H); 3.06 (bt, 4H); 3.62 (bt, 4H); 5.10 (bs, 1H); 5.75 (bs, 1H); 6.09 (d, 1H); 6.45 (bs, 1H); 7.05 (bs, 1H); 7.11 (t, 2H); 7.32–7.46 (m, 5); 7.66 (dd, 2H); 8.21 (d, 1H).

MS (m/z) ESI: 495 (MH+, 100).

The compounds of Examples 15–17 are similarly prepared:

Example 15

2-(4-Fluorophenyl)-1-(2-cyclopentylamino-4-pyrimidinyl)-5-(4-NH-1-piperazinyl)imidazo[4,5-b]pyridine:

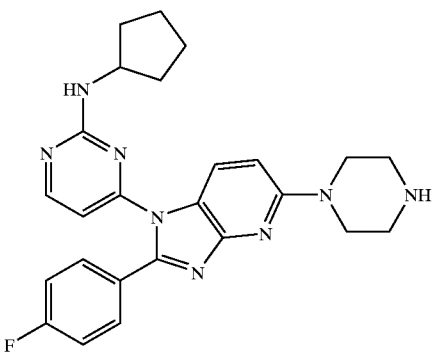

1H-NMR (400 MHz; DMSO-d6, 120° C.): 1.43–1.58 (m, 4H); 1.65–1.75 (m, 2H); 1.80–1.90 (m, 2H); 3.10 (t, 4H); 3.73 (t, 4H); 4.00–4.08 (m, 1H); 6.38 (d, 1H); 6.90 (d, 1H); 6.95 (bd, 1H, NH); 7.26 (t, 2H); 7.68 (dd, 2H); 7.96 (d, 1H); 8.34 (d, 1H).

MS (m/z) ESI: 459.3 (MH+, 100).

Example 16

2-(4-Fluorophenyl)-1-(2-cyclobutylamino4-pyrimidinyl)-5-(4-NH-1-piperazinyl)imidazo[4,5-b]pyridine:

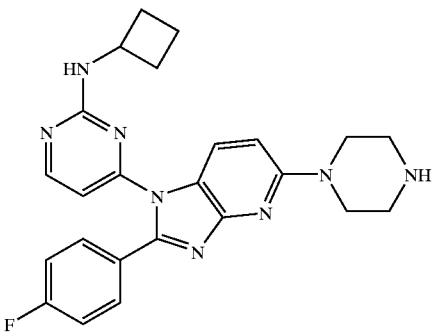

1H-NMR (400 MHz; CDCl3): 1.65–1.89 (m, 4H); 1.91–2.05 (m, 2H); 2.43 (bs, 1H); 3.06 (t, 4H); 3.67 (t, 4H); 4.40 (bs, 1H, NH); 5.50 (bd, 1H, NH); 6.17 (bd, 1H); 6.75 (d, 1H); 7.11 (t, 2H); 7.68 (dd, 2H); 7.97 (d, 1H); 8.23 (d, 1H).

MS (m/z) ESI: 445.3 (MH+, 100).

Example 17

2-(4-Fluorophenyl)-1-(2-cyclopropylamino-4-pyrimidinyl)-5-(4-NH-1-piperazinyl)imidazo[4,5-b]pyridine:

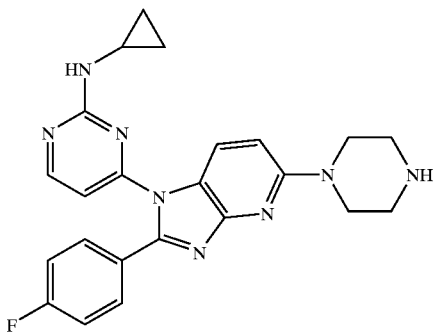

1H-NMR (400 MHz; DMSO-d6): 0.47 (bs, 2H); 0.62 (bs, 2H); 2.33 (bs, 1H); 2.83 (bt, 4H); 3.47 (bt, 4H); 6.34 (bs, 1H); 6.92 (d, 1H, NH); 7.36 (t, 2H); 7.65 (dd, 2H); 7.85 (bd, 1H); 8.10 (bs, 1H); 8.36 (bd, 1H).

MS (m/z) ESI: 431.2 (MH+, 100).

Example 18

2-(4-Fluorophenyl)-1-(2-(1-(S)-phenylethyl)amino-4-pyrimidinyl)-5-(4methyl-1-piperazinyl)imidazo[4,5-b]pyridine

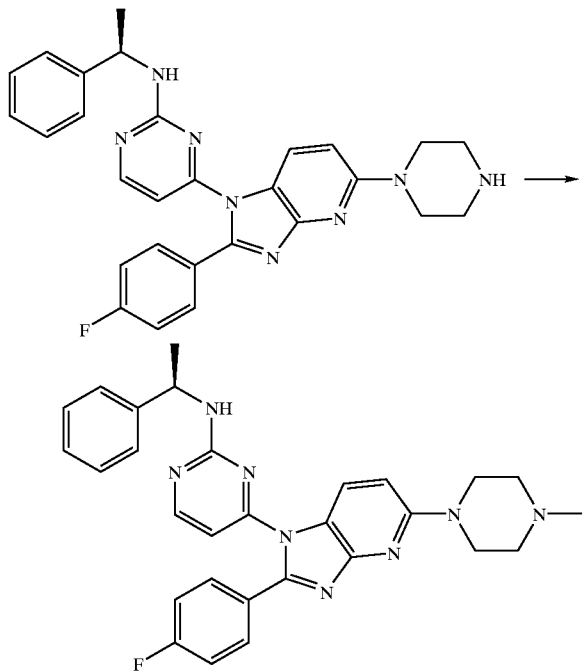

2-(4-Fluorophenyl)-1-(2-(1-(S)-phenylethyl)amino-4-pyrimidinyl)-5-(4-methyl-1-piperazinyl)imidazo[4,5-b]pyridine (50 mg, 0.1 mmol) is dissolved in MeOH (2.5 ml). An aqueous 36%-solution of formaldehyde (15.8 ml, 0.2 mmol) is added and stirred for 30 min. NaBH (7.5 mg, 0.2 mmol) is added and stirring continued for 30 min. The reaction mixture is poured on water and extracted with ethyl acetate three times. The combined organic phases are dried over Na₂SO₄, filtered and evaporated to dryness. Purification over SiO₂ (tert.-butyl methyl ether/MeOH/NH₃conc 90/9/1) yields the title compound as a yellow powder (35 mg 68%) 1H-NMR (400 MHz; CDCl₃): 1.61 (d, 3H); 2.40 (s, 3H); 2.60 (bt, 4H); 3.68 (bt, 4H); 5.12 (m, 1H); 5.76 (bs, 1H, NH); 6.08 (d, 1H); 6.48 (bs 1H); 7.10 (t, 2H); 7.35–7.46 (m, 6H); 7.66 (dd, 2H); 8.21 (d, 1H).

MS (m/z) ESI: 509 (MH+, 100).

The compounds of Examples 19–21 are similarly prepared:

Example 19

2-(4-Fluorophenyl)-1-(2-cyclopentylamino-4-pyrimidinyl)-5-(4-methyl-1-piperazinyl)imidazo[4,5-b]pyridine:

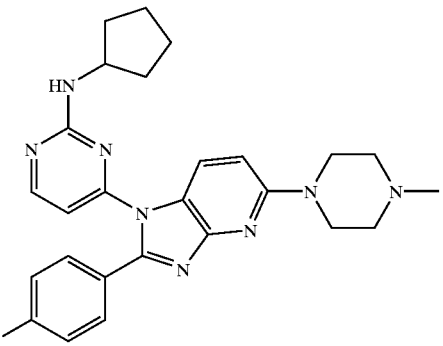

1H-NMR (400 MHz; DMSO-d6): 1.45–1.58 (m, 2H); 1.61–1.83 (m, 4H); 1.97–2.13 (m, 2H); 2.38 (s, 3H); 2.59 (t, 4H); 3.71 (t, 4H); 4.10–4.31 (m, 1H); 5.33 (bd, 1H, NH), 6.16 (bs, 1H); 6.75 (d, 1H); 7.11 (t, 2H); 7.68 (dd, 2H); 7.97 (d, 1H); 8.23 (d, 1H).

MS (m/z) ESI: 473.3 (MH+, 100).

Example 20

2-(4-Fluorophenyl)-1-(2-cyclobutylamino-4-pyrimidinyl)-5-(4-methyl-1-piperazinyl)imidazo[4,5-b]pyridine:

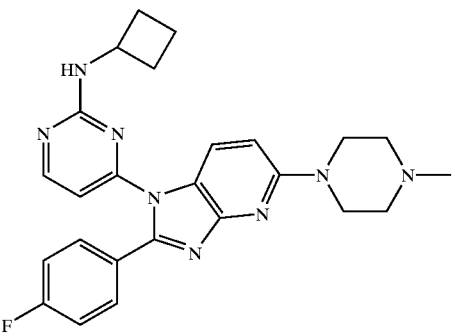

1H-NMR (400 MHz; DMSO-d6): 1.45–2.12 (m, 6H); 2.20 (m, 1H); 2.25 (s, 3H); 2.45 (bt, 4H); 3.55 (bt, 4H); 6.95 (bs, 1H); 7.32 (t, 2H); 7.62 (bs, 2H); 7.93 (bd, 2H); 8.33 (bs, 1H);

MS (m/z) ESI: 459.3 (MH+, 100).

Example 21

2-(4-Fluorophenyl)-1-(2-cyclopropylamino-4-pyrimidinyl)-5-(4-methyl-1-piperazinyl)imidazo[4,5-b]pyridine:

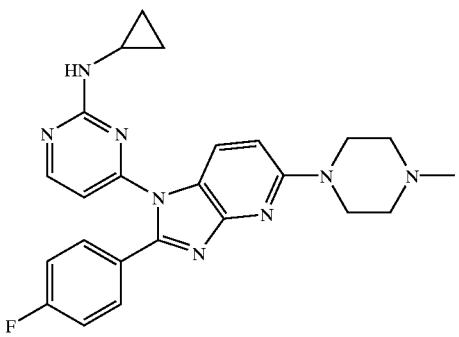

1H-NMR (400 MHz; CDCl3): 0.64 (m, 2H); 0.88 (m, 2H); 2.38 (s, 3H); 2.58 (t, 4H); 2.82 (bs, 1H); 3.72 (t, 4H); 5.58 (s, 1H, NH); 6.19 (d, 1H); 6.74 (d, 1H); 7.13 (t, 2H); 7.71 (dd, 2H); 8.12 (bs, 1H); 8.28 (bs, 1H).

MS (m/z) ESI: 445 (MH+, 100).

Example 22

2-(4Fluorophenyl)-1-(2-(1-(S)-phenylethyl)amino-4-pyrimidinyl)-5-(4-(2-hydroxy-2-methyl)propyl-1-piperazinyl)imidazo[4,5-b]pyridine

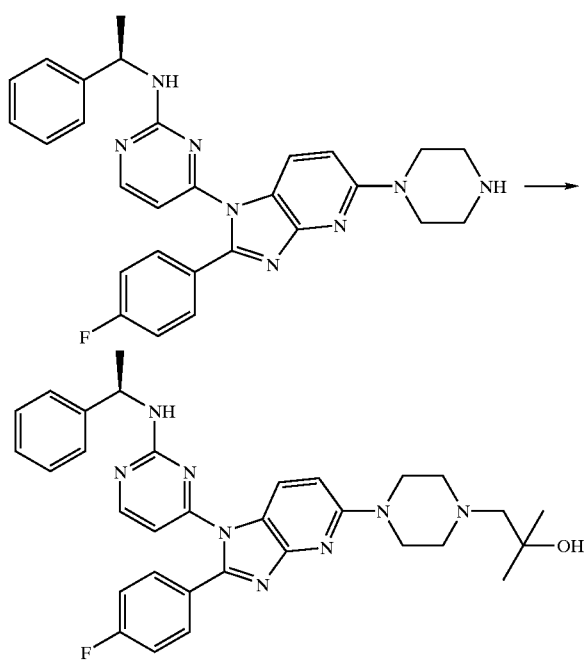

2-(4-Fluorophenyl)-1-(2-(1-(S)-phenylethyl)amino-4-pyrimidinyl)-5-(4-NH-1-piperazinyl)imidazo [4,5-b]pyridine (60 mg, 0.12 mmol) and isobutyleneoxide (43.5 ml 0.6 mmol) in EtOH (6 ml) are heated at 80° C. for 3 h. The reaction mixture is evaporated and purified by SiO2 chromatography (tert.-butyl methyl ether/MeOH/NH3conc. 97/2.7/0.3) to yield the title compound as a yellow foam (40 mg 60%).

1H-NMR (400 MHz; DMSO, 120° C.): 1.18 (s, 6H); 1.48 (d, 3H); 2.43 (s, 2H); 2.72 (dd, 4H); 3.58 (dd, 4H); 5.10 (m, 1H); 6.32 (d, 1H); 6.73 (d, 1H); 7.21 (t, 2H); 7.28–7.38 (m, 5H); 7.43 (bd, 1H, NH); 7.62 (dd, 2H); 7.65 (d, 1H); 8.32 (d, 1H).

MS (m/z) ESI: 567 (MH+, 100).

The compounds of Examples 23–25 are similarly prepared:

Example 23

2-(4-Fluorophenyl)-1-(2-cyclopentylamino-4-pyrimidinyl)-5-(4-(2-hydroxy-2-methyl)propyl-1-piperazinyl)imidazo[4,5-b]pyridine

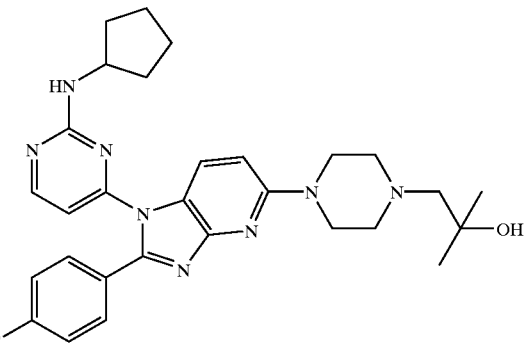

1H-NMR (400 MHz; DMSO): 1.24 (s, 6H); 1.52 (bs, 2H); 1.67 (bs, 2H); 1.79 (bs, 2H); 2.08 (bs, 2H); 2.42 (s, 2H); 2.82 (bt, 4H); 3.20 (bs, 1H, OH); 3.70 (bt, 4H); 4.22 (bs, 1H); NH); 6.17 (bs, 1H); 6.74 (d, 1H); 7.12 (t, 2H); 7.70 (dd, 2H); 7.97 (d, 1H); 8.23 (d, 1H)

MS (m/z) ESI: 531.3 (MH+, 100).

Example 24

2-(4-Fluorophenyl)-1-(2-cyclobutylamino-4-pyrimidinyl)-5-(4-(2-hydroxy-2-methyl)propyl-1-piperazinyl)imidazo[4,5-b]pyridine

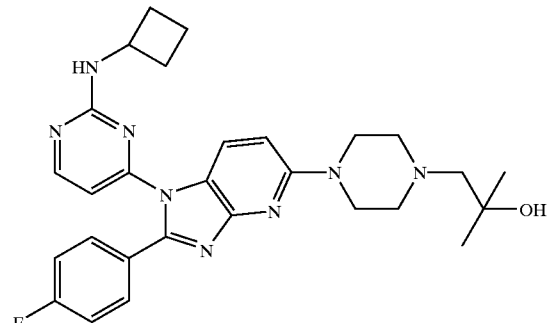

1H-NMR (400 MHz; DMSO): 1.25 (s, 6H); 1.56–2.03 (m, 6H); 2.43 (s, 2H); 2.82 (t, 4H); 3.15 (bs, 1H, OH); 3.70 (t, 4H); 4.40 (bs, 1H, NH); 5.50 (bd, 1H, NH); 6.15 (bs, 1H); 6.74 (d, 1H); 7.12 (t, 2H); 7.69 (dd, 2H); 7.98 (d, 1H); 8.25 (d, 1H).

MS (m/z) ESI: 517.4 (MH+, 35).

Example 25

2-(4-Fluorophenyl)-1-(2-cyclopropylamino-4-pyrimidinyl)-5-(4-(2-hydroxy-2-methyl)propyl-1-piperazinyl)imidazo[4,5-b]pyridine

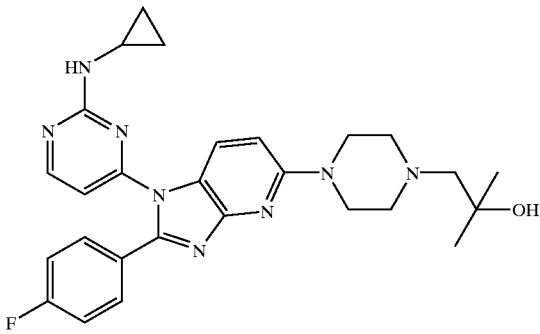

1H-NMR (400 MHz; DMSO): 0.64 (m, 2H); 0.88 (m, 2H); 1.25 (s, 6H); 2.42 (s, 2H); 2.83 (m, 5H); 3.17 (s, 1H, OH); 3.70 (bt, 4H); 5.57 (s, 1H, NH); 6.20 (d, 1H); 6.73 (d, 1H); 7.13 (t, 2H); 7.71 (dd, 2H); 8.12 (bs, 1H); 8.29 (bs, 1H).
MS (m/z) ESI: 503.3 (MH+, 40).

Example 26

2-(4-Fluorophenyl)-1-(2-cyclopentylamino-4-pyrimidinyl)-5-(4-piperidinyl)imidazo[4,5-b]pyridine

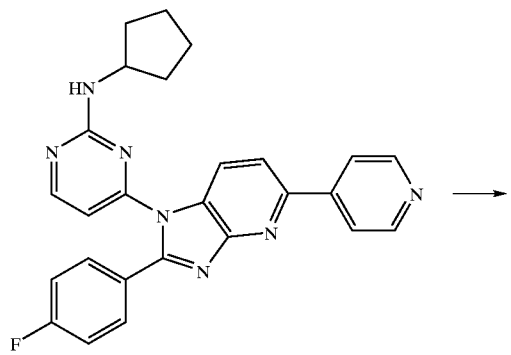

2-(4-Fluorophenyl)-1-(2-cyclopentylamino-4-pyrimidinyl)-5-(4-pyridinyl)imidazo[4,5-b]pyridine (example 7; 100 mg; 0.22 mmol) is dissolved in HOAc (120 ml) and hydrogenated over Pd/C (10%, 200 mg) in a Parr apparatus for 48 h at room temperature. The reaction mixture is filtered and evaporated to dryness delivering the title compound as yellow crystals, which are recrystallised from MeOH and gave the title compound as colorless crystals (70 mg; 65%).

1H-NMR (400 MHz; DMSO-d6, 120° C.): 1.49 (m, 4H); 1.68. (m, 2H); 1.83 (m, 2H); 2.10 (m, 4H); 3.05 (dt, 4H); 3.18 (m, 1H); 3.48 (m, 4H); 4.03 (m, 1H); 6.45 (d, 1H); 7.05 (bd, 1H, NH); 7.30 (m, 2H); 7.70 (m, 2H); 8.08 (d, 1H); 8.40 (d, 1H).

MS (m/z) ESI: 458.3 (MH+; 100).

Example 27

2-(4-Fluorophenyl)-1-(2-cyclopentylamino-4-pyrimidinyl)-5-(1-methyl-4-piperidinyl)imidazo[4,5-b]pyridine

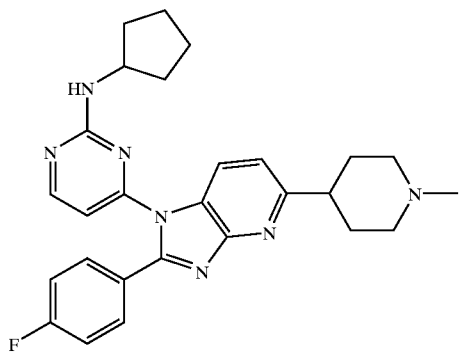

The title compound is prepared in analogy to Example 18.

MS (m/z) ESI: 472.4 (MH+, 100).

Example 28

2-(4-Fluorophenyl)-1-(2cyclopentylamino-4-pyrimidinyl)-5(1-(2-hydroxy-2-methyl)propyl-4-piperidinyl)imidazo[4,5-b]pyridine

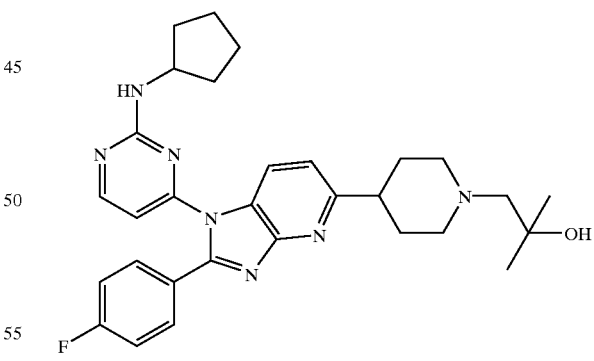

The title compound is prepared in analogy to Example 22.

1H-NMR (400 MHz; DMSO-d6, 120° C.): 1.21 (s, 6H); 1.43–1.83 (m, 8H); 1.95–2.18 (m, 5H); 2.41 (s, 2H); 2.56 (bt, 2H); 2.88 (bt, 1H); 3.08 (bd, 2H); 5.37 (bs, 1H, NH); 6.21 (bs, 1H); 7.13 (t, 2H); 7.21 (d, 1H); 7.72 (dd, 2H); 8.06 (d, 1H); 8.28 (d, 1H).

MS (m/z) ESI: 530 (MH+, 100)

Example 29

2-(4-Fluorophenyl)-1-(2-cyclopentylamino-4-pyrimidinyl)-5-(benzylamino)imidazo[4,5-b]pyridine

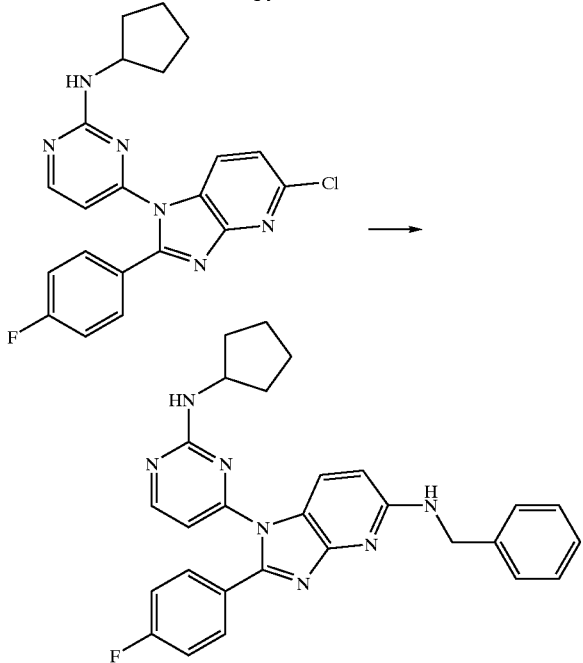

2-(4-Fluorophenyl)-1-(2-cyclopentylamino-4-pyrimidinyl)-5-(chloro)imidazo[4,5-b]pyridine (100 mg; 0.25 mmol), R-(+)-BINAP (10 mg; 0.016 mmol), Pd$_2$(dba)$_3$ (22 mg; 0.024 mmol) are suspended in xylene (16 ml), benzylamine (0.53 ml; 4.9 mmol) is added, followed by NaOtBu (47 mg; 0.49 mmol) and heated to 160° C. for 10 min. under argon. The reaction mixture is poured on water (100 ml) containing HOAc (2 ml) and extracted with TBME three times. The combined organic phases are washed with 2N Na$_2$CO$_3$, dried over Na$_2$SO$_4$ and evaporated to dryness. Purification via SiO$_2$ chromatography (TMBE/hexane 6:4 to 10:0) and recrystallisation from TBME yields the title compound as colorless crystals (50 mg: 50%).

1H-NMR (400 MHz; CDCl$_3$): 1.45–1.85 (m, 6H); 1.95–2.13 (m, 2H); 4.25 (bs, 1H); 4.72 (d, 1H); 4.86 (bt, 1H, NH); 5.31 (bd, 1H, NH); 6.15 (bs, 1H); 6.43 (d, 1H); 7.11 (t, 2H); 7.28 (m, 3H); 7.35 (t, 2H); 7.45 (d, 1H); 7.68 (dd, 2H); 7.89 (d, 1H); 8.23 (d, 1H).

MS (m/z) ESI: 480 (MH+, 100).

Example 30

2-(4-Fluorophenyl)-1-(2-cyclopentylamino-4-pyrimidinyl-5-(morpholino)imidazo[4,5-b]pyridine

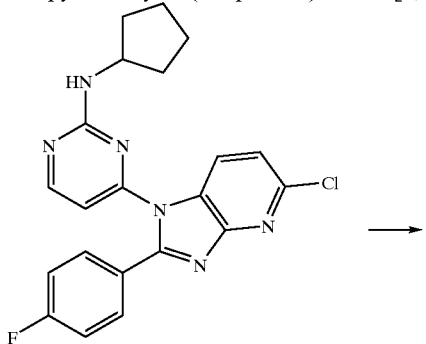

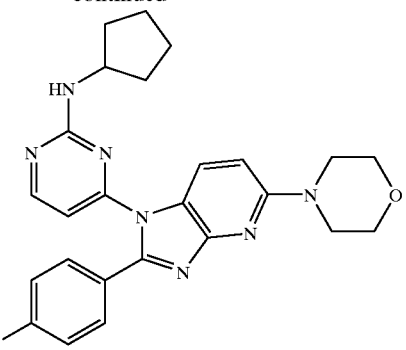

2-(4-Fluorophenyl)-1-(2-cyclopentylamino-4-pyrimidinyl)-5-(chloro)imidazo[4,5-b]pyridine (10 mg; 0.25 mmol), R-(+)-BINAP (10 mg; 0.016 mmol), Pd$_2$(dba)$_3$ (22 mg; 0.024 mmol) are suspended in xylene (16 ml), morpholine (0.43 ml; 4.9 mmol) is added, followed by NaOtBu (47 mg; 0.49 mmol) and heated to 160° C. for 10 min. under argon. The reaction mixture is poured on water (100 ml) containing HOAc (2 ml) and extracted with TBME three times. The combined organic phases are washed with 2N Na$_2$CO$_3$, dried over Na$_2$SO$_4$ and evaporated to dryness. Purification via SiO$_2$ chromatography (TBME/hexane 7:3 to 10:0) and recrystallisation from TBME yields the title compound as colorless crystals (22 mg: 19%).

1H-NMR (400 MHz; CDCl$_3$): 1.47–1.84 (m, 6H); 1.97–2.17 (bs, 2H); 3.65 (m, 4H); 3.88 (m, 4H); 4.22 (bs, 1H); 5.33 (bs, 1H, NH); 6.16 (bs, 1H); 6.72 (d, 1H); 7.11 (t, 2H); 7.69 (dd, 2H); 8.00 (d, 1H); 8.25 (bd, 1H).

MS (m/z) ESI: 460 (MH+, 100).

Example 31

2-(4-Fluorophenyl)-1-(2-cyclopentylamino-4-pyrimidinyl)-5-(3-fluorophenyl amino)imidazo[4,5-b]pyridine The title compound is prepared in analogy to Example 29

-continued

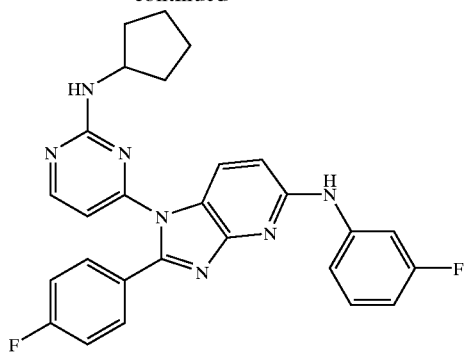

1H-NMR (400 MHz, CDCl₃): 1.48–1.87 (m, 6H); 1.95–2.18 (m, 2H); 4.22 (s, 1H); 5.37 (bs, 1H, NH); 6.15 (bs, 1H); 6.72 (bs, 2H); 6.86 (d, 1H); 7.15 (t, 2H); 7.28 (m, 2H); 7.53 (d, 1H); 7.70 (dd, 2H); 8.03 (d, 1H); 8.27 (d, 1H).

MS (m/z) ESI: 484 (MH+, 100).

Example 32

2-(4-Fluorophenyl)-1-(2-cyclopentylamino-4-pyrimidinyl)-5-(pyridyl-4-amino)imidazo[4,5-b]pyridine The title compound is prepared in analogy to Example 29.

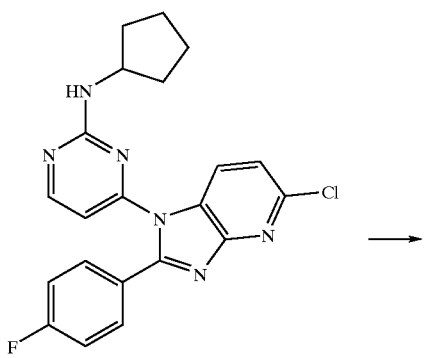 

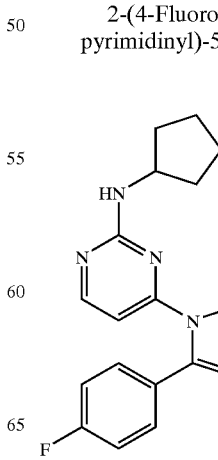

1H-NMR (400MHz, CDCl₃): 1.47–1.93 (m, 6H); 1.97–2.20 (m, 2H); 4.22 (m, 1H); 5.40 (d, 1H, NH); 6.17 (bs, 1H); 6.93 (d, 1H); 7.18 (m, 2H); 7.71 (m, 4H); 8.12 (d, 1H); 8.42 (d, 2H).

MS (m/z) ESI: 467 (MH+, 100).

Example 33

2-(4-Fluorophenyl)-1-(2-cyclopentylamino-4-pyrimidinyl)-5-(1-ethoxycarbonyl piperidine-4-amino)imidazo[4,5-b]pyridine The title compound is prepared in analogy to Example 29

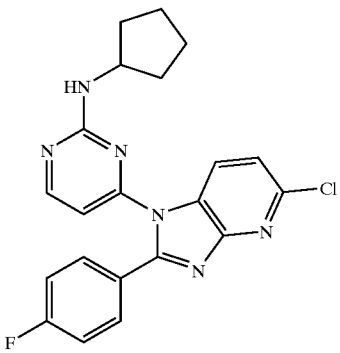 

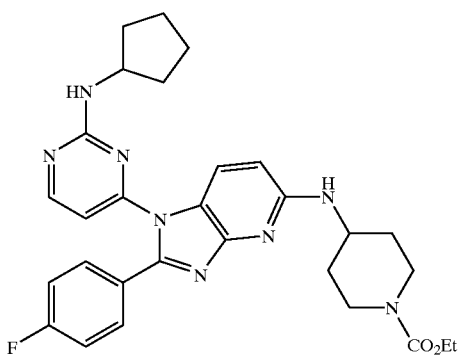

1H-NMR (400 MHz, CDCl₃): 1.31 (t, 3H); 1.38–1.85 (m, 10H); 1.93–2.13 (bs, 1H); 2.21 (bd, 2H); 3.05 (bt, 2H); 4.03–4.39 (m, 4H); 5.33 (bs, 1H, NH); 6.15 (bs, 1H); 6.40 (d, 1H); 7.11 (t, 2H); 7.66 (dd, 2H); 7.88 (d, 1H); 8.23 (d, 1H).

MS (m/z) ESI: 545 (MH+, 100).

Example 34

2-(4-Fluorophenyl)-1-(2-cyclopentylamino-4-pyrimidinyl)-5-(piperidine-4-amino)imidazo[4,5-b]pyridine

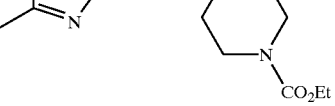 

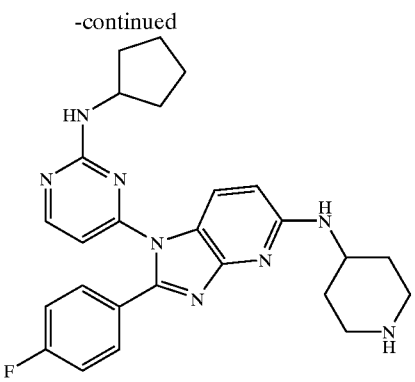

2-(4-Fluorophenyl)-1-(2-cyclopentylamino-4-pyrimidinyl)-5-(1-ethoxycarbonylpiperidine-4-amino) imidazo[4,5-b]pyridine (58 mg; 0.1 mmol) is dissolved in CHCl$_3$ (2 ml) and treated with trimethylsilyliodide (0.3 ml; 2.2 mmol) in a sealed vessel at 60° C. for 5 h. 6N HCl in isopropanol is added to the reaction mixture, which is then poured on 2N Na$_2$CO$_3$/2N NaOH and extracted with CH$_2$Cl$_2$ three times. The combined organic phases are dried over Na$_2$SO$_4$ and evaporated to dryness to yield the crude title compound, which is purified via recrystallisation from THF/TBME (44 mg; 88%).

1H-NMR (400 MHz, CDCl$_3$): 1.35–1.82 (m, 8H); 2.06 (bs, 2H); 2.22 (bd, 2H); 2.82 (bt, 2H); 3.15 (bd, 2H); 4.06–4.32 (m, 3H); 4.39 (d, 1H, NH); 5.32 (bd, 1H, NH); 6.14 (bs, 1H); 6.38 (d, 1H); 7.10 (t, 2H); 7.66 (dd, 2H); 7.87 (d, 1H); 8.23 (d, 1H).

MS (m/z) ESI: 473.1 (MH+, 100).

The Agents of the Invention, as defined above, e.g., of formula I, II and V particularly as exemplified, in free or pharmaceutically acceptable acid addition salt form, exhibit pharmacological activity and are useful as pharmaceuticals, e.g. for therapy, in the treatment of diseases and conditions as hereinafter set forth.

In particular Agents of the Invention possess p38 MAP kinase (Mitogen Activated Protein Kinase) inhibiting activity. Thus the Agents of the Invention act to inhibit production of inflammatory cytokines, such as TNF-α and IL-1, and also to potentially block the effects of these cytokines on their target cells. These and other pharmacological activities of the Agents of the Invention as may be demonstrated in standard test methods for example as described below:

p38 MAP Kinase Assay

The substrate (GST-ATF-2; a fusion protein comprising amino acids 1–109 of ATF-2 and the GST protein obtained by expression in *E. coli*) is coated onto the wells of microtiter plates (50 μl/well; 1 μg/ml in PBS/0.02% Na azide) overnight at 4 ° C. The following day, the microliter plates are washed four times with PBS/0.5% Tween 20/0.02% Na azide and are blocked with PBS/2% BSA/0.02% Na Azide for 1 h at 37 ° C. Plates are washed again 4 times with PBS/0.5% Tween 20/0.02% Na azide. The kinase cascade reaction is then started by adding the following reactants in 10 μl aliquots to a final reaction volume of 50 μl.

1. Agents of the Invention titrated from 10 to 0.001 μM in 10-fold dilutions or solvent (DMSO) or H$_2$O.
2. Kinase buffer (5×); pH 7.4; 125 mM Hepes (Stock at 1M; Gibco #15630-056), 125 mM β-glycerophosphate (Sigma #G-6251): 125 mM MgCl$_2$ (Merck #5833); 0.5 mM Sodium orthovanadate (Sigma #5-6508), 10 mM DTT (Boehringer Mannheim #708992). The (5×) kinase buffer must be prepared fresh the day of the assay from 5× stock solutions kept at RT. DTT is kept at −20° C. and is added as the last reagent.
3. His-p38 MAP kinase (10 ng/well; Novartis—a fusion protein comprising full length murine p38 MAP kinase and a His tag, obtained by expression in *E. coli*)
4. cold ATP (final concentration 120 μM; Sigma #A-9187)
5. Water After 1 h at 37° C. the kinase reaction is terminated by washing the plates four times as previously described. Phosphorylated GST-ATF-2 is then detected by adding:

1. the PhosphoPlus ATF-2 (Thr71) Antibody (50 μl/well; 1/1000 final dilution in PBS/2% BSA/0.02% Na Azide; New England Biolabs #9221L) for 90 min at RT.
2. Biotin labelled goat-anti-rabbit IgG (50 μl/well; 1/3000 final dilution in PBS/2% BSA/0.02% Na Azide; Sigma #B-9642) for 90 min at RT.
3. Streptavidin-alkaline phosphatase (50 μl/well; 1/5000 dilution in PBS/2% BSA/0.02% Na Azide; Jackson Immunoresearch #016-050-084 ) for 30 min at RT.
4. Substrate (100 μl/well; Sigma 104 Phosphatase substrate tablets, 5 mg/tablet; #104–105; 1 mg/ml in substrate buffer, Diethanolamine (97 ml/l; Merck #803116)+MgCl$_2$.6H$_2$O (100 mg/l; Merck #5833)+Na Azide (0.2 g/l)+HCl 1M to pH 9.8) 30 min at RT.

After step 1,2 and 3 the microtiter plates are washed four times with PBS/0.5% Tween 20/0.02% Na azide. After step 4, the plates are read in a Bio-Rad microplate reader in a dual wavelength mode (measurement filter 405 nm and reference filter 490 nm). The background value (without ATP) is subtracted and IC$_{50}$ values are calculated using the Origin computer program (4 parameter logistic function).

Agents of the Invention typically have IC$_{50}$s for p38 MAP kinase inhibition in the range from about 100 nM to about 5 nM or less when tested in the above assay.

Assay for Inhibition of TNF-α Release from hPBMCs

Human peripheral blood mononucleer cells (hPBMCs) are prepared from the peripheral blood of healthy volunteers using ficoll-hypaque density separation according to the method of Hansel et al., J. Imm. Methods (1991) 145: 105. and used at a concentration of 10$^5$ cells/well in RPMI 1640 plus 10% FCS. Cells are incubated with serial dilutions of the test compounds for 30 minutes at 37° C. prior to the addition of IFNg (100 U/ml) and LPS (5 mg/ml) and subsequently firer incubated for three hours. Incubation is terminated by centrifugation at 1400 RPM for 10 min. TNF-α in the supernatant is measured using a commercial ELISA (Innotest hTNFa, available from Innogenetics N.V., Zwijnaarde, Belgium). Agents of the Invention are tested at concentrations of from 0 to 10 mM. Exemplified Agents of the Invention typically suppress TNF release in this assay with an IC$_{50}$ of from about ? nM to about ? nM or less when tested in this assay.

Assay for Inhibition of TNF-α Production in LPS Stimulated Mice

Injection of lipopolysaccharide (LPS) induces a rapid release of soluble tumour necrosis factor (TNF-α) into the periphery. This model is be used to analyse prospective blockers of TNF release in vivo.

LPS (20 mg/kg) is injected i.v. into OF1 mice (female, 8 week old). One (1) hour later blood is withdrawn from the animals and TNF levels are analysed in the plasma by an ELISA method using an antibody to TNF-α. Using 20 mg/kg of LPS levels of up to 15 ng of TNF-α/ml plasma are usually induced. Compounds to be evaluated are given either orally or s.c. 1 to 4 hours prior to the LPS injection. Inhibition of LPS-induced TNF-release is taken as the readout.

Agents of the Invention typically inhibit TNF production to the extent of up to about 50% or more in the above assay when administered at 10 mg/kg p.o.

As indicated in the above assays Agents of the Invention are potent inhibitors of TNF-α release. Accordingly, the Novel Compounds have pharmaceutical utility as follows:

Agents of the Invention are useful for the prophylaxis and treatment of diseases or pathological conditions mediated by cytokines such as TNFα and IL-I, e.g., inflammatory conditions, autoimmnune diseases, severe infections, and organ or tissue transplant rejection, e.g. for the treatment of recipients of heart, lung, combined heart-lung, liver, kidney, pancreatic, skin or corneal transplants and for the prevention of graft-versus-host disease, such as following bone marrow transplants.

Agents of the Invention are particularly useful for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases. Specific auto-immune diseases for which Agents of the Invention may be employed include autoimmune haematological disorders (including e.g. hemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Agents of the Invention are also useful for the treatment, prevention, or amelioration of asthma, bronchitis, pneumoconiosis, pulmonary emphysema, and other obstructive or inflammatory diseases of the airways.

Agents of the Invention are useful for treating undesirable acute and hyperacute inflammatory reactions which are mediated by TNF, especially by TNFα, e.g., acute infections, for example septic shock (e.g., endotoxic shock and adult respiratory distress syndrome), meningitis, pneumonia; and severe burns; and for the treatment of cachexia or wasting syndrome associated with morbid TNF release, consequent to infection, cancer, or organ dysfunction, especially AIDS-related cachexia, e.g., associated with or consequential to HIV infection.

Agents of the Invention are also useful for the treatment of neurodegenerative diseases, such as Alzheimer's disease, acute encephalitis, brain injury, multiple sclerosis including demyelation and oligiodendrocyte loss in multiple sclerosis and inflammatory nervous system diseases. such as neuroinflammatory and stroke.

Agents of the Invention are particularly useful for treating diseases of bone metabolism including osteoarthritis, osteoporosis and other inflammatory arthritides.

For the above indications the appropriate dosage will, of course, vary depending, for example, on the particular Agent of the Invention employed, the subject to be treated, the mode of administration and the nature and severity of the condition being treated. However, in general, satisfactory results in animals are obtained at daily dosages of from about 1 to about 10 mg/kg/day p.o. In larger mammals, for example humans, an indicated daily dosage is in the range of from about 50 to about 750 mg of an Agent of the Invention administered orally once or, more suitably, in divided dosages two to four times/day.

The Agents of the Invention may be administered by any conventional route, e.g. orally, for example in the form of solutions for drinking, tablets or capsules or parenterally, for example in the form of injectable solutions or suspensions. Normally for systemic administration oral dosage forms are preferred, although for some indications the Agents of the Invention may also be administered topically or dermally, e.g. in the form of a dermal cream or gel or like preparation or. for the purposes of application to the eye, in the form of an ocular cream, gel or eye-drop preparation; or may be administered by inhalation, e.g., for treating asthma. Suitable unit dosage forms for oral administration comprise e.g. from 25 to 250 mg of Agent of the Invention per unit dosage.

In accordance with the foregoing the present invention also provides in a further series of embodiments:

A. A method of inhibiting production of soluble TNF, especially TNFα, or of reducing inflammation in a subject (i.e., a mammal, especially a human) in need of such treatment which method comprises administering to said subject an effective amount of an Agent of the Invention, or a method of treating any of the above mentioned conditions, particularly a method of treating an inflammatory or autoimmnune disease or condition, e.g. rheumatoid arthritis, or alleviating one or more symptoms of any of the above mentioned conditions.

B. An Agent of the Invention for use as a pharmaceutical, e.g. for use as an immunosuppressant or antiinflammatory agent or for use in the prevention, amelioration or treatment of any disease or condition as described above, e.g., an autoimmune or inflammatory disease or condition.

C. A pharmaceutical composition comprising an Agent of the Invention in association with a pharmaceutically acceptable diluent or carrier, e.g., for use as an immunosuppressant or anti-inflammatory agent or for use in the prevention, amelioration or treatment of any disease or condition as described above, e.g., an autoimmune or inflammatory disease or condition.

D. Use of an Agent of the Invention in the manufacture of a medicament for use as an immunosuppressant or anti-inflammatory agent or for use in the prevention, amelioration or treatment of any disease or condition as described above, e.g., an autoimmune of inflammatory disease or condition.

What is claimed is:

1. A compound of formula (I)

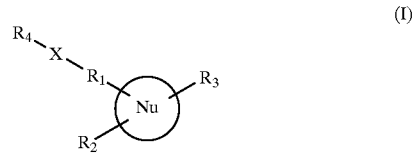

(I)

wherein Nu is a heterocyclic nucleus selected from thiazole in which the $R_1$, $R_2$ and $R_3$ substituents are disposed as indicated below

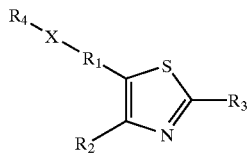

wherein
R₁ is pyrimidyl or pyridyl;
X is —NR₆—Y—, —O— or —S—;
where
R₆ is H,
C₁–C₄alkyl, C₃–C₈cycloalkyl, C₃–C₈cycloalkylC₁–C₃alkyl, C₆–C₁₈aryl, C₃–C₁₈heteroaryl, C₇–C₁₉aralkyl or C₄–C₁₉heteroaralkyl, and —Y— is C₁–C₄alkylene or a direct bond;
R₂ is phenyl, optionally substituted by one or more substituents, each of which is independently selected from
Halo,
CF₃,
Cyano,
amido or thioamido, which is optionally mono- or di-N-substituted by C₁–C₄alkyl or the N atom of which forms a 5- to 7-membered heterocyclic ring optionally having an additional hetero atom selected from O, S or N, which N is optionally C₁–C₄alkyl C₁–C₄alkylcarbonyl or C₁–C₄alkylthiocarbonyl substituted;
carboxylate or thiocarboxylate,
optionally in the form of an optionally halo-substituted C₁–C₁₀alkoxy, C₂–C₁₀alkenoxy, C₂–C₁₀alkynoxy, C₃–C₇cyclalkoxy, C₅–C₇cycloalkenoxy, aryloxy, arylalkoxy, heteroaryloxy or heteroarylalkoxy ester,
optionally mono- or di-C₁–C₄alkyl-substituted- C₀–C₁alkyl optionally C₁–C₄alkyl- or C₃–C₅cycloalkyl-substituted-carbonyl or -thiocarbonyl,
optionally halo-substituted-C₁–C₄alkoxy, C₂–C₄alkenoxy, C₂–C₄alkynoxy, C₃–C₅cycloalkoxy or C₃–C₅cyclothioalkoxy,
optionally halo substituted C₁–C₄alkyl;
oxycarbonyl or optionally N—C₁–C₄alkyl-substituted aminocarbonyl both of which are optionally C₁–C₄alkyl or C₃–C₅cycloalkyl substituted,
optionally mono- or di-C₁–C₄alkyl-substituted- C₀–C₁alkylamine which is optionally mono- or di-N—C₁–C₄alkyl substituted,
optionally mono- or di-C₁–C₄alkyl-substituted- C₀–C₁alkyl optionally N—C₁–C₄alkyl-substituted amino-carbonyl or -thiocarbonyl,
optionally N—C₁–C₄alkyl-substituted amino-sulphinyl or -sulphonyl optionally substituted by optionally mono- or di-N—C₁–C₄alkyl-substituted amino,
a nitrogen atom which forms a heterocyclic ring of 5 to 7 members optionally having an additional heteroatom selected from O, S or N, which N is optionally C₁–C₄alkyl C₁–C₄alkylcarbonyl or C₁–C₄alkylthiocarbonyl substituted; or
sulphinyl or sulphonyl optionally substituted by
optionally halo-substituted-C₁–C₄alkyl, C₂–C₄alkenyl, C₂–C₄alkynyl,
optionally mono- or di-C₁–C₄alkyl-substituted amino,
a nitrogen atom which form a heterocyclic ring of 5 to 7 members optionally having an additional heteroatom selected from O, S or N, which N is optionally C₁–C₄alkyl C₁–C₄alkylcarbonyl or C₁–C₄alkylthiocarbonyl substituted;
R₃ is H, amino, C₁–C₁₀alkyl, C₃–C₁₀cycloalkyl, C₃–C₁₈heterocycloalkyl, C₆–C₁₈aryl, or C₃–C₁₈heteroaryl each of which is optionally substituted by up to 4 substituents separately selected from C₁–C₄alkyl, halogen, halo-substitued-C₁–C₄alkyl, hydroxy, C₁–C₄alkoxy, C₁–C₄alkylthio, C₆–C₁₈aryl, C₃–C₁₈heteroaryl, C₆–C₁₈arylC₁–C₄alkyl, C₃–C₁₈heteroarylC₁–C₄alkyl, C₃–C₁₈heterocycloalkyl or optionally mono- or di-C₁–C₄alkyl substituted amino or by N-heterocyclyl having from 5- to 7-ring atoms and optionally a further hetero atom selected from O, S or N, all of which are further optionally substituted halo, hydroxy, C₁–C₄alkyl, C₁–C₄alkoxy or C₁–C₄alkoxycarbonyl; and
R₄ is C₁–C₁₀alkyl, C₆–C₁₈aryl, C₃–C₁₈heteroaryl, or C₃–C₁₂cycloalkyl optionally substituted by up to 3 substituents separately selected from C₁–C₄alkyl, halogen, halo-substitued-C₁–C₄alkyl, hydroxy, C₁–C₄alkoxy, C₁–C₄alkylthio, optionally mono- or di-C₁–C₄alkyl substituted amino, or by N-heterocyclyl having from 5- to 7-ring atoms and optionally having a further hetero atom selected from O, S or N;
or pharmaceutically-acceptable esters thereof, or acid addition salts thereof, or, when said compound comprises one or more free hydroxyl groups, the pharmaceutically-acceptable prodrug esters thereof, which are cleavable under physiological conditions to release the compound having one or more free hydroxyl groups.

2. A compound according to claim 1 of formula (II)

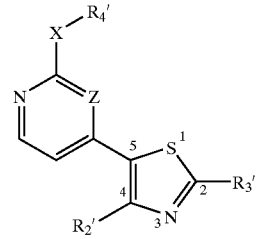

(II)

wherein
Z is N or CH;
X is —NR₆—Y—, —O— or —S—,
where
R₆ is H, C₁–C₄alkyl, C₃–C₈cycloalkyl, C₃–C₈cycloalkylC₁–C₃alkyl, C₆–C₁₈aryl, C₃–C₁₈heteroaryl C₇–C₁₉aralkyl or C₄–C₁₉heteroaralkyl; and
—Y— is C₁–C₄alkylene or a direct bond;
R₂' is phenyl, optionally substituted by one or more substituents, each of which is, independently, selected from halo, CF₃, cyano, amido or thioamido, carboxylate or thiocarboxylate, C₁–C₄alkoxy, C₁–C₄alkyl or NH₂, which is optionally mono- or di-C₁–C₄alkyl substituted;
R₃' is H, C₁–C₁₀alkyl, C₃–C₁₀cycloalkyl, C₃–C₁₈heterocycloalkyl, C₆–C₁₈aryl or C₃–C₁₈heteroaryl each of which is optionally substituted by up to 4 substituents separately selected from C₁–C₄alkyl, halogen, halo-substitued-C₁–C₄alkyl, hydroxy, $C_1$–$C_4$alkoxy, $C_1$–$C_4$alkylthio or optionally mono- or di- $C_1$–$C_4$alkyl substituted amino, or by N-heterocyclyl having from 5- to 7-ring atoms and optionally having a further hetero atom selected from O, S or N;

$R_4{}'$ is $C_6$–$C_{18}$aryl, $C_3$–$C_{18}$heteroaryl or $C_3$–$C_{12}$cycloalkyl each of which is optionally substitute by up to 4 substituents separately selected from $C_1$–$C_4$alkyl, halogen, halo-substituted-$C_1$–$C_4$alkyl, hydroxy, $C_1$–$C_4$alkoxy, $C_1$–$C_4$alkylthio, or optionally mono- or di-$C_1$–$C_4$alkyl substituted amino, or by N-heterocyclyl having from 5- to 7-ring atoms and optionally having a further hetero atom selected from O, S or N, or pharmaceutically-acceptable esters thereof, or acid addition salts thereof, or, when said compound comprises one or more free hydroxyl groups, the pharmaceutically-acceptable prodrug esters thereof, which are cleavable under physiological conditions to release the compound having one or more free hydroxyl groups.

3. A compound according to claim 2 of formula (II')

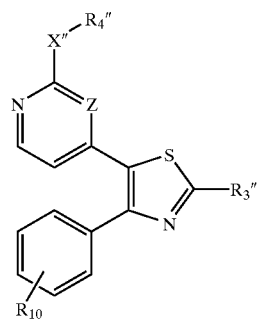

(II')

wherein
$R_4{}''$ is phenyl or $C_3$–$C_7$cycloalkyl each of which is optionally mono-substituted by halogen, $C_1$–$C_4$alkyl, $C_1$–$C_4$alkoxy, hydroxy, trihalomethyl optionally mono- or di-$C_1$–$C_4$alkyl substituted amino, or by N-heterocyclyl having from 5- to 7-ring atoms and optionally having a further hetero atom selected from O, S or N;

$R_{10}$ is halogen, cyano, amido, thioamido, amino or $C_1$–$C_4$alkyl;

$R_3{}''$ is H, $C_1$–$C_4$alkyl, phenyl, pyridyl, morpholinyl, piperidyl, piperazyl or optionally mono- or di-$C_1$–$C_4$alkyl substituted amino, each of which is optionally substituted, by up to 2 substituents, separately selected from $C_1$–$C_4$alkyl, halogen, hydroxy, $C_1$–$C_4$alkoxy or optionally mono- or di-$C_1$–$C_4$alkyl substituted amino;

Z is N or CH; and

X" is —NH—Y'—, —O— or —S—, where Y' is —$CH_2$—, —$CH_2$—$CH_2$—, —$CH(CH_3)$— or a direct bond;

or pharmaceutically-acceptable esters thereof, or acid addition salts thereof, or, when said compound comprises one or more free hydroxyl groups, the pharmaceutically-acceptable prodrug esters thereof, which are cleavable under physiological conditions to release the compound having one or more free hydroxyl groups.

4. A compound according to claim 2, selected from:
4-(4-Fluorophenyl)-5-(2-[1-(S)-phenylethyl]amino-4-pyrimidinyl)-2-(4-methyl-piperidine-1-yl)thiazole;
4-(4-Fluorophenyl)-5-(2-[1-(S)-phenylethyl]amino-4-pyrimidinyl)-2-(4-NH-piperdine-1-yl)thiazole;
4-(4-Fluorophenyl)-2-(4-methylpiperidine-1-yl)-5-(2-[cyclopropyl-methyl]amino-4-pyridinyl)thiazole and
4-(4-Fluorophenyl)-2-(4-NH-piperidine-1-yl)-5-(2-(1-(S)-phenylethyl)amino-4-pyridinyl)thiazole;

or pharmaceutically-acceptable esters thereof, or acid addition salts thereof, or, when said compound comprises one or more free hydroxyl groups, the pharmaceutically-acceptable prodrug esters thereof, which are cleavable under physiological conditions to release the compound having one or more free hydroxyl groups.

5. A process for the preparation of a compound of formula (II'')

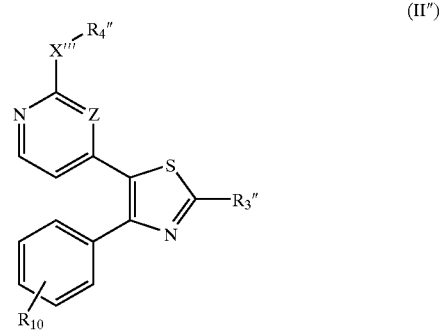

(II'')

wherein
$R_3{}''$, $R_4{}''$, $R_{10}$ and Z are as defined in claim 3; and
X''' is —NH—, which comprises reacting the corresponding precursor compound of formula (III) or (III')

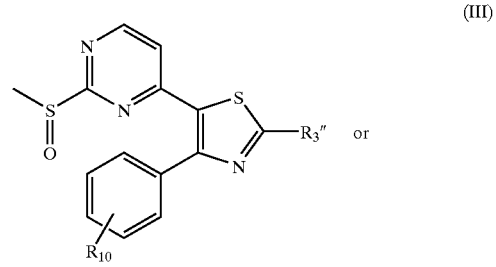

(III)

or

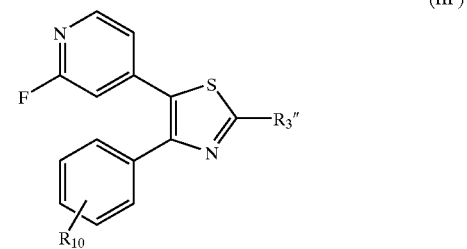

(III')

with the corresponding $R_4{}'$—$NH_2$ amine, wherein $R_3{}'$, $R_4{}''$ and $R_{10}$ are as defined in claim 3, and thereafter, if desired, converting the compound of formula (II'') obtained into a further compound of formula (II'');

or pharmaceutically-acceptable esters thereof, or acid addition salts thereof, or, when said compound comprises one or more free hydroxyl groups, the pharmaceutically-acceptable prodrug esters thereof, which are cleavable under physiological conditions to release the compound having one or more free hydroxyl groups.

6. A pharmaceutical composition comprising a compound according to claim 1 in association with a pharmaceutically acceptable diluent or carrier.

7. A method of inhibiting production of soluble TNF or of reducing inflammation in a subject in need of such treatment which method comprises administering to said subject an effective amount of a compound according to claim 1.

8. The method of claim 7, wherein the soluble TNF is TNFα.

9. The method of claim 7, wherein the subject is a mammal.

10. The method of claim 9, wherein the mammal is a human.

* * * * *

UNITED STATES PATENT AND TRADEMARK OFFICE
CERTIFICATE OF CORRECTION

PATENT NO.   : 6,608,072 B1                                      Page 1 of 1
DATED        : August 19, 2003
INVENTOR(S)  : Laszlo Revesz It is certified that error appears in the above-identified patent and that said Letters Patent is hereby corrected as shown below:

Column 57,
Line 6, should read -- each of which is optionally substituted by up to 4 --

Column 58,
Line 55, should read -- with the corresponding $R_4'$—$NH_2$ amine, wherein $R_3''$, $R_4''$ --

Signed and Sealed this

Twenty-first Day of October, 2003

JAMES E. ROGAN
*Director of the United States Patent and Trademark Office*